US012788290B2

(12) United States Patent
Korecky et al.

(10) Patent No.: US 12,788,290 B2

(45) Date of Patent: Nov. 10, 2026

(54) APPARATUS AND A METHOD FOR THE EXTRACTION AND COLLECTION OF BODILY FLUIDS

(71) Applicant: SiPhox, Inc., Burlington, MA (US)

(72) Inventors: Pavel Korecky, New York City, NY (US); Colin Budries, Burlington, MA (US); Sidarth Kulkarni, Boston, MA (US)

(73) Assignee: SiPhox, Inc., Burlington, MA (US)

( * ) Notice: Subject to any disclaimer, the term of this patent is extended or adjusted under 35 U.S.C. 154(b) by 197 days.

(21) Appl. No.: 18/916,025

(22) Filed: Oct. 15, 2024

(65) Prior Publication Data

US 2025/0120627 A1 Apr. 17, 2025

Related U.S. Application Data

(60) Provisional application No. 63/590,064, filed on Oct. 13, 2023.

(51) Int. Cl.

*A61B 5/15* (2006.01)
*A61B 5/151* (2006.01)

(52) U.S. Cl.

CPC .. *A61B 5/150099* (2013.01); *A61B 5/150022* (2013.01); *A61B 5/150183* (2013.01); *A61B 5/150229* (2013.01); *A61B 5/150343* (2013.01); *A61B 5/150412* (2013.01); *A61B 5/15117* (2013.01); *A61B 5/15186* (2013.01)

(58) Field of Classification Search

None
See application file for complete search history.

(56) References Cited

U.S. PATENT DOCUMENTS

| | | | |
|---|---|---|---|
| 9,757,095 B2 | 9/2017 | Terbrueggen et al. | |
| 2004/0236251 A1* | 11/2004 | Roe | A61B 5/150022 600/583 |
| 2010/0056954 A1 | 3/2010 | Oren | |
| 2010/0261988 A1* | 10/2010 | Tamir | A61B 5/150519 600/583 |
| 2016/0287219 A1* | 10/2016 | Zhao | A61F 9/00736 |
| 2017/0035336 A1* | 2/2017 | Wilkinson | A61B 5/150786 |
| 2017/0332954 A1* | 11/2017 | Hsiung | A61B 5/150343 |
| 2020/0253521 A1* | 8/2020 | Ivosevic | A61B 5/150022 |
| 2022/0225912 A1 | 7/2022 | Nieuwborg et al. | |

FOREIGN PATENT DOCUMENTS

| | | |
|---|---|---|
| JP | 2019047893 A | 3/2022 |

* cited by examiner

*Primary Examiner* — Etsub D Berhanu
(74) *Attorney, Agent, or Firm* — CALDWELL LLC

(57) ABSTRACT

An apparatus for the extraction and collection of bodily fluids is disclosed. The apparatus includes a housing configured to receive a body part, wherein the housing comprises an upper portion and a lower portion. The housing includes an end cap removably attached to the upper portion of the housing, wherein the end cap comprises a ribbed connector. The housing additionally includes a first aperture located on the lower portion of the housing. The apparatus includes a gasket mechanically attached to the lower portion of the housing. The apparatus includes a suction device fluidically connected to the ribbed connector of the end cap using a hose. The apparatus includes a fluid collection device configured to extract bodily fluids from the body part as a function of the negative pressure environment, wherein the fluid collection device is removably attached to the end cap.

20 Claims, 13 Drawing Sheets

APPARATUS AND A METHOD FOR THE EXTRACTION AND COLLECTION OF BODILY FLUIDS

CROSS-REFERENCE TO RELATED APPLICATIONS

This application claims the benefit of priority of U.S. Provisional Patent Application Ser. No. 63/590,064, filed on Oct. 13, 2023, and titled "BODILY FLUID COLLECTION ASSISTANCE DEVICE," which is incorporated by reference herein in its entirety.

FIELD OF THE INVENTION

The present invention generally relates to the field of medical equipment. In particular, the present invention is directed to an apparatus and a method for the extraction and collection of bodily fluids.

BACKGROUND

Gathering and testing samples of bodily fluids from a user has long been a painful and unpleasant task. Thus, new methods/systems to gather and test samples are needed.

SUMMARY OF THE DISCLOSURE

In an aspect, an apparatus for the extraction and collection of bodily fluids is disclosed. The apparatus includes a housing configured to receive a body part, wherein the housing comprises an upper portion and a lower portion. The housing includes an end cap removably attached to the upper portion of the housing, wherein the end cap comprises a ribbed connector. The housing additionally includes a first aperture located on the lower portion of the housing. The apparatus includes a gasket mechanically attached to the lower portion of the housing, wherein the gasket is configured to form an airtight seal between the body part and the housing. The apparatus includes a suction device fluidically connected to the ribbed connector of the end cap using a hose, wherein the suction device is configured to create a negative pressure environment within the housing. The apparatus includes a fluid collection device configured to extract bodily fluids from the body part as a function of the negative pressure environment, wherein the fluid collection device is removably attached to the end cap.

In another aspect, a method for the extraction and collection of bodily fluids is disclosed. The method includes receiving, using a housing comprising an upper portion and a lower portion, a body part. The housing further includes an end cap removably attached to the upper portion of the housing, wherein the end cap comprises a ribbed connector. The housing also includes a first aperture located on the lower portion of the housing. The method includes mechanically attaching a gasket to the lower portion of the housing, wherein the gasket is configured to form an airtight seal between the body part and the housing. The method includes fluidically connecting, using a hose, a suction device to the ribbed connector of the end cap, wherein the suction device is configured to create a negative pressure environment within the housing. The method includes extracting, using a fluid collection device, bodily fluids from the body part as a function of the negative pressure environment, wherein the fluid collection device is removably attached to the end cap.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

Figure 1A:
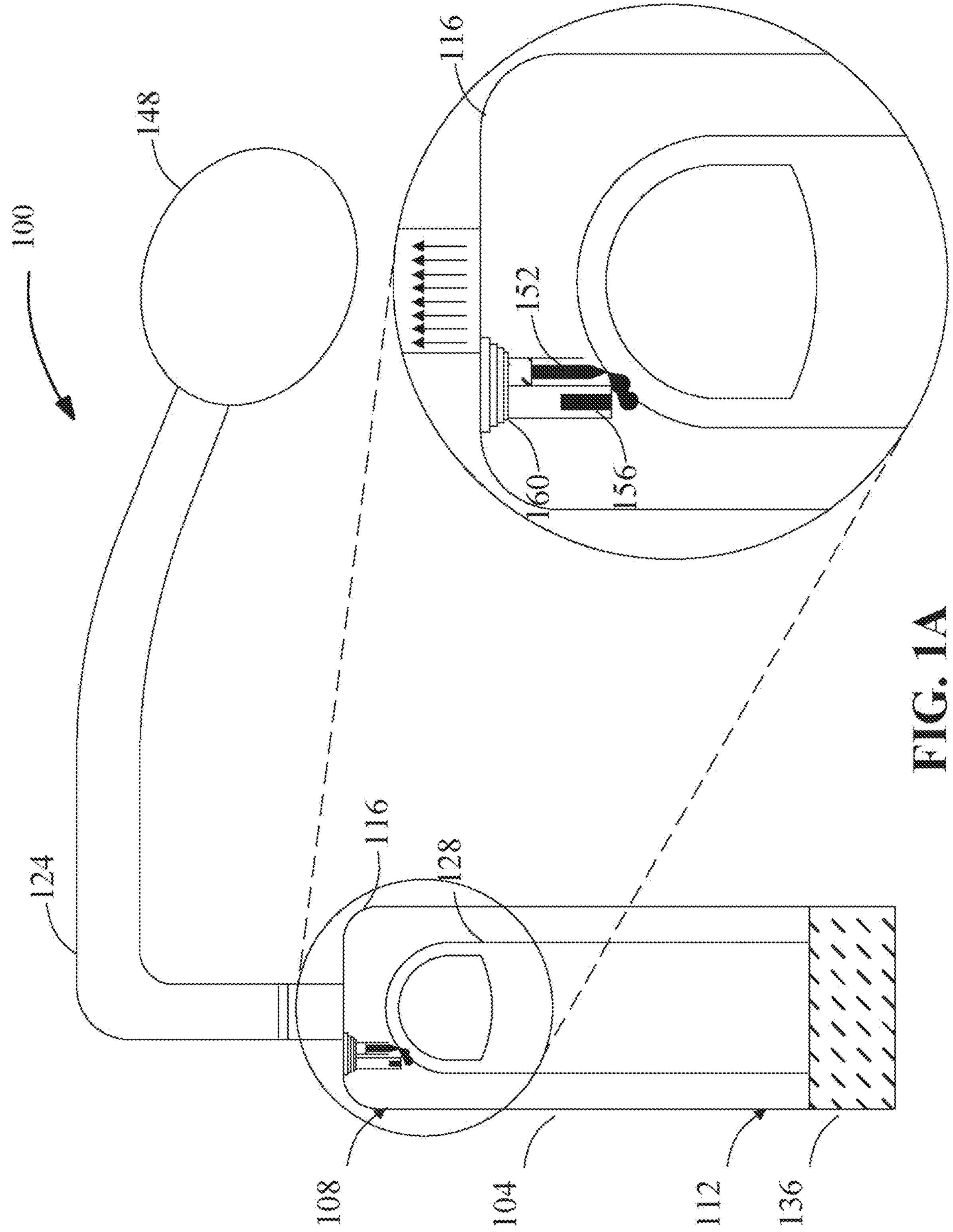
FIGS. 1A-G are illustrations of an exemplary embodiment of an apparatus for the extraction and collection of bodily fluids.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to an apparatus and a method for the extraction and collection of bodily fluids is disclosed. The apparatus includes a housing configured to receive a body part, wherein the housing comprises an upper portion and a lower portion. The housing includes an end cap removably attached to the upper portion of the housing, wherein the end cap comprises a ribbed connector. The housing additionally includes a first aperture located on the lower portion of the housing. The apparatus includes a gasket mechanically attached to the lower portion of the housing, wherein the gasket is configured to form an airtight seal between the body part and the housing. The apparatus includes a suction device fluidically connected to the ribbed connector of the end cap using a hose, wherein the suction device is configured to create a negative pressure environment within the housing. The apparatus includes a fluid collection device configured to extract bodily fluids from the body part as a function of the negative pressure environment, wherein the fluid collection device is removably attached to the end cap. Exemplary embodiments illustrating aspects of the present disclosure are described below in the context of several specific examples.

Referring now to FIGS. 1A-G, an exemplary embodiment of an apparatus 100 for the extraction and collection of bodily fluids is illustrated. Apparatus 100 includes a housing 104. As used in the current disclosure, a "housing" is an enclosure intended to accommodate a specific part of the human body. The housing 104 may additionally house a fluid collection device, a lancet, one or more gaskets, along with other mechanical components disclosed within this application. The housing 104 may include an upper portion 108 and a lower portion 112. The upper portion 108 is the portion of the housing near the end cap. In an embodiment, a hose and suction device may be fluidly connected to the upper portion of the housing. In an embodiment, the upper portion 108 of the housing may be enclosed using the end cap, whereas the lower portion of the housing may not be enclosed due to the first aperture. The lower portion 112 of the housing is the portion of the housing that is portion of the housing near the first aperture. The lower portion 112 of the housing may be configured to receive the body part using the first aperture. When mated with the body part, the housing 104 may be configured to be hermetically sealed. This may mean that an airtight connection is formed between the body part and the housing 104. This may be done to create a negative pressure environment within the housing during the fluid collection process. As used in the current disclosure, a "negative pressure environment" refers to a space where the air pressure is lower than the pressure in the surrounding areas. The negative pressure environment inside of the housing 104 may be configured to suction out bodily fluids from the body part. In an embodiment, the housing 104 may take a three-dimensional form. This may include the housing 104 having a cylindrical geometry, rectangular prism geometry, conical geometry, and the like. A cylindrical geometry may be characterized by its uniform circular cross-section along its length. In a non-limiting example, a housing 104 may have a length between 5 cm to 15 cm or between 9 cm and 11 cm. In some cases, a housing 104 may have a length of 10 cm. In an embodiment, the diameter of the housing may be 3.5 cm. The diameter of the housing may also be between 2 cm and 10 cm or between 3 cm and 4 cm. The exterior walls of the housing may have a thickness of between 0.1 cm and 0.5 cm or between 0.15 cm and 0.25 cm. In some cases, the thickness of the exterior walls of the housing may be 0.2 cm With continued reference to FIG. 1B, housing 104 may be made of metal or durable plastic. Housing 104 may be made of one or more medical grade plastics. Examples of medical grade plastics may include polycarbonate, ABS (Acrylonitrile Butadiene Styrene), and polypropylene. These plastics may be resistant to many chemicals and can be molded into ergonomic shapes for easy handling. In an embodiment, portions of housing 104 may be made of stainless steel. Housing 104 may be made of glass-filled nylon. In an additional embodiment, the housing 104 may be made of transparent materials to allow the user to observe the body part while it is within the housing 104. This may be done to facilitate the fluid collection process.

Figure 1C:
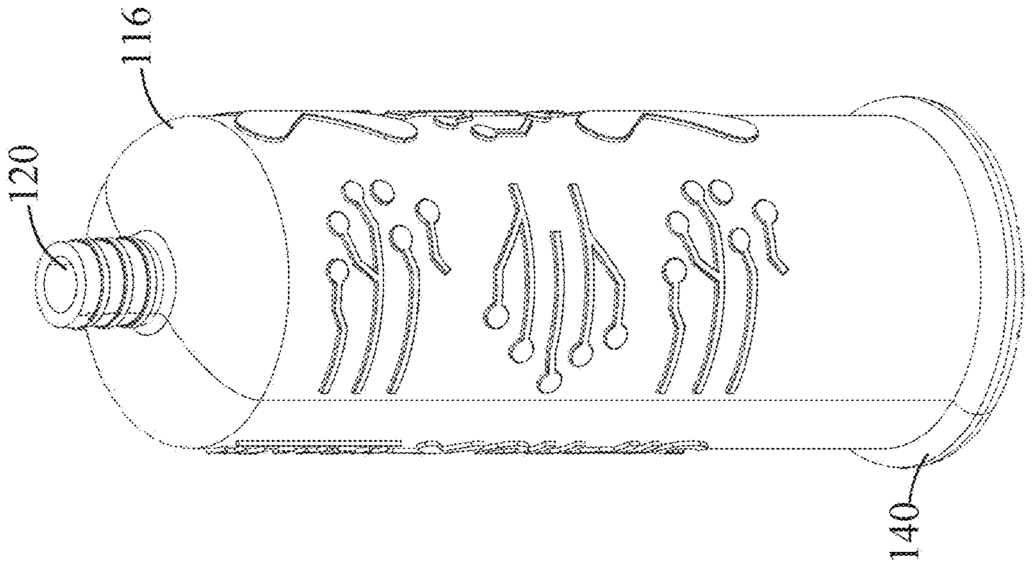
Figure 1B:
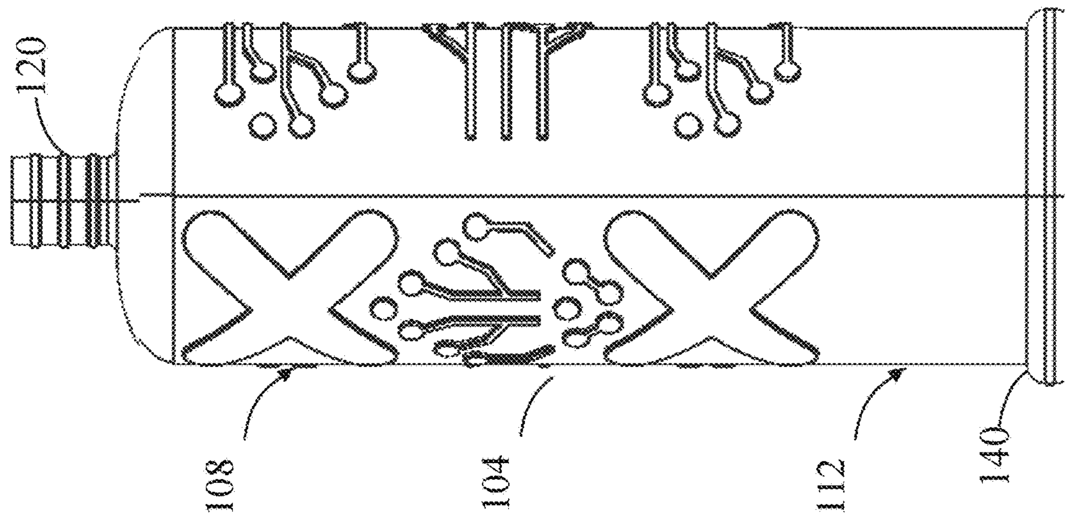

With continued reference to FIGS. 1B-C, the housing 104 may include one or more end caps 116 located on the upper portion 108 of the housing 104. As used in the current disclosure, an "end cap" is a covering for an end portion a housing 104. By covering this end, the end cap 116 may seal the interior of the housing. When in place, the end cap 116 may provide a secure airtight seal. This could be important for maintaining a controlled environment within the housing, such as a sterile area, a vacuum, or a specific atmospheric composition The end cap 116 of the housing may be used to selectively cover an opening at the upper portion of the housing. This may mean that the end cap 116 may be either secured in place to close off the housing or removed/opened to provide access to the interior portion of the end cap 116. The end cap 116 of a housing 104 may be located at the upper portion 108 of the housing 104. The end cap of the housing 104 may be permanently attached to the housing 104. Alternatively, the end cap 116 may be removably attached to the housing 104. For the purposes of this disclosure, "removably attached" refers to an ability for an object that is connected to another object to be disconnected from the other object without damaging or breaking said objects.

With continued reference to FIGS. 1A-C, an end cap 116 may include an interior portion and an exterior portion. The interior portion of the end cap 116 is the portion of the end cap that faces the interior of the housing when the end cap is mated to the upper portion 108 of the housing 104. The exterior portion of the end cap is portion of the end cap 116 that faces away from the housing 104. The selective attachment of the end cap 116 to the housing 104 may facilitate easy access to the interior of the end cap 116. This may be important to collect bodily fluids from the fluid collection device, sterilize the end cap 116, and change the lancet. In an embodiment, the interior portion of the end cap 116 may be configured to mate with the fluid collection device and the lancet. Each of these instruments may be configured to be inserted into a mating component located on the interior portion of the end cap 116.

With continued reference to FIGS. 1B-C, the end cap 116 may additionally include a ribbed connector 120. As used in the current disclosure, a "ribbed connector" is a type of attachment mechanism that allows a secure, removable connection between two components using one or more ribs. The ribbed connector 120 may fluidly connect the housing 104 and the end cap 116 to a hose 124 and a suction device 148. The ribbed connector 120 may be fluidly connected to the interior portion of the housing 104. In an embodiment, ribbed connector 120 may be used to remove air from the housing 104 to create the negative pressure environment. The ribbed connector 120 may be configured to have a three-dimensional geometry. This may include a cylindrical geometry, conical geometry, rectangular prism geometry, and the like. The ribbed connector 120 may have a ribbed surface that protrudes from the exterior portion of the connector. These ribs may include circular ridges that run around the circumference of the connector. The ribs may provide extra grip and a better seal when inserted into the hose. The elasticity of the hose material allows it to conform to the shape of the ribs, creating a tighter fit. To connect the ribbed connector 120 to a hose, the ribbed end of the connector may be inserted into the end of a hose. The hose may expand slightly to accommodate the ribs and then tightens around them, creating a secure connection. In some embodiments, a hose clamp or similar device is used in conjunction with the ribbed connector 120 to ensure the hose does not slip off, especially in applications where there is pressure in the hose. In an embodiment, the ribbed connector 120 may have an external diameter between 0.5 cm and 1.5 cm or 0.7 cm and 1 cm, whereas the ribbed connector may also have an internal diameter between 0.3 cm and 0.75 cm or between 0.5 cm and 0.7 cm. In some cases, the ribbed connector 120 may have an external diameter of 0.9 cm and an internal diameter of 0.6 cm. The ribbed connector may be configured to have a height between 1 cm and 2.5 cm or between 1 cm and 2 cm. This may include the ribbed connector having a height of 1.5 cm.

With continued reference to FIGS. 1A-C, the upper portion 108 of the housing 104 may be configured to selectively mate with the end cap 116 using one or more mating connections. The mating connection between the housing 104 and the end cap 116 may be configured to form a hermetic seal. As used in the current disclosure, a "mating connection" refers to a physical connection between two or more components. A mating connection may require a male component and a female component The mating connection may include a threaded connection, snap-fit connection, friction fit, magnetic connection, latch, and hook, interlocking joint, and the like. The mating connection between an end of the housing and the upper portion of the housing may be configured to have an airtight seal. In an embodiment, a gasket or O-ring may be placed between the male component and female component to facilitate an airtight seal. The O-ring may be seated in a groove on either the end cap 116 or the upper portion 108 of the housing 104. When the two parts are joined, the O-ring may be compressed forming an airtight seal between the end cap 116 and the upper portion of the housing.

With continued reference to FIG. 1A, the ribbed connector 120 may be fluidly connected to a hose 124. As used in the current disclosure, a "hose" is a conduit for air or fluids being drawn out of the housing by the suction device. The hose may be made out of flexible materials like rubber, plastic, or reinforced composites to withstand the pressure changes and potential abrasion during the suction process. The size and length of the hose may vary depending on the size of the housing 104 and the configuration of the suction device that is connected to the hose 124. The hose may be in fluidic communication with the ribbed connector 120 and the suction device. As used in the current disclosure, "fluidic communication" refers to the ability of fluids (liquids or gases) to move or be transferred between different parts or components of a system. The terms fluidic communication and fluidic connection may be used interchangeably throughout the entirety of this disclosure. This may be used to describe how fluids flow or are directed through apparatus 100. When two or more components are said to be in fluidic communication, it may mean that there is a pathway or connection that allows for the free passage of fluids between them. This can involve channels, hoses, valves, pumps, suction devices, connector, or other mechanisms that facilitate the movement of the fluid.

With continued reference to FIG. 1A, the housing 104 is configured to receive a body part 128 within the first aperture. As used in the current disclosure, a "body part" is a distinct section or portion of a human body. A body part may include any protruded body part that is able to fit within the housing. A protruded body part is a part of the body that extends outward and can be easily isolated or identified. This may include fingers, toes, hands, feet, arms, and the like. The body part 128 may be selectively inserted within the housing. The body part 128 may be configured to extend to the upper portion of the housing and make contact with the lancet and the fluid collection device.

Figure 1G:
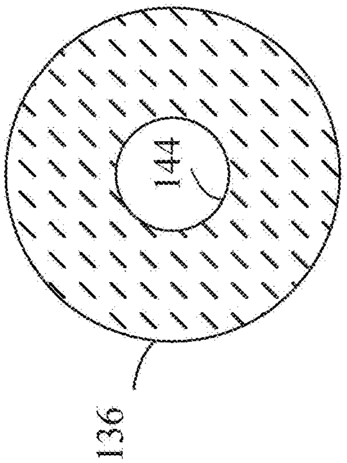
Figure 1E:
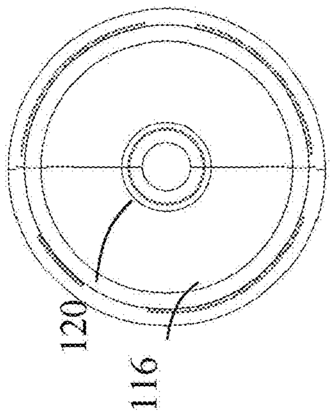
Figure 1F:
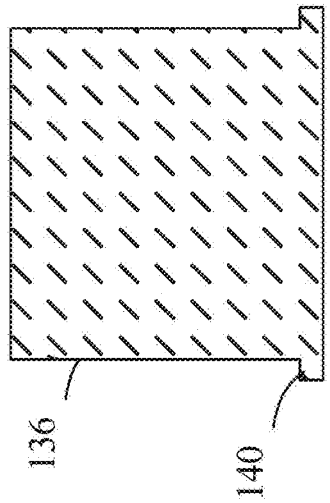
Figure 1D:
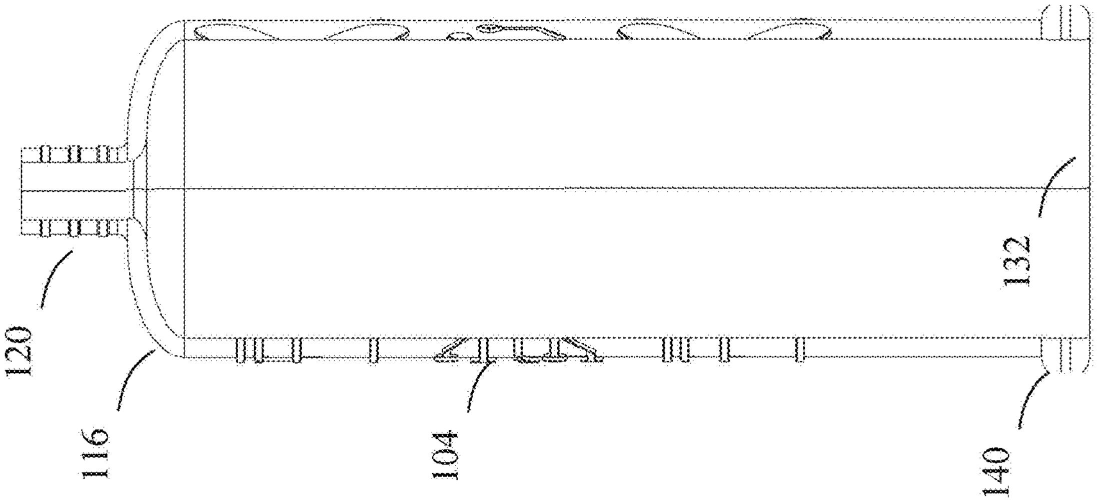

With continued reference to FIG. 1D, the lower portion 112 of the housing includes a first aperture 132. As used in the current disclosure, a "first aperture" is an opening located on the lower portion of the housing. The first aperture 132 may provide access to the interior of the housing 104. The first aperture may have a diameter that is long enough to accommodate a body part 128. In an embodiment, the aperture may have a circular geometry. In an embodiment, the first aperture 132 might have adjustable an adjustable diameter to accommodate different sizes of the same body part. This may involve mechanisms like straps, expandable openings, or inserts that can be added or removed for better fit and comfort.

With continued reference to FIG. 1F-G, apparatus 100 includes a gasket 136 mechanically attached to the first aperture 132. As used in the current disclosure, a "gasket" is a mechanical seal which fills the space between two or more surfaces to create an airtight seal. The gasket 136 may be configured to fill the space between the first aperture 132 and the body part. The gasket 136 may be made of flexible materials, such as silicone, rubber, neoprene, and other elastomeric compounds. The gasket 136 may be configured to conform to the contours of both the housing 104 and the body part 128. In a non-limiting example, when the body part is inserted into the housing 104, the gasket 136 deforms slightly, filling any gaps and preventing air from entering or escaping. This compression may ensure that no air passes through. In an embodiment, the gasket 136 may be configured to extend up the side of the housing 104. The gasket 136 may extend up the side of the housing between 1 cm and 5 cm or between 2 cm and 3 cm. The gasket 136 may be configured to extend up the side of the housing 2.5 cm. The gasket 136 may be configured mate with a protruded brim 140 of the housing. As used in the current disclosure, a "protruded brim" is a design feature that extends outward from the main body of the housing 104, creating an overhanging edge or lip. The protruded brim 140 may be designed to stick out beyond the main body or profile of the housing, forming a noticeable edge or rim. The protruded brim 140 may serve as an anchor point for the gasket 136. The gasket 136 may be configured to cover the protruded brim 140 and extend up the side of the housing to form an airtight seal. The protruded brim 140 may be used to create a seal with another with the gasket 136. In an embodiment, the protruded brim may protrude from the housing 104 between 0.01 cm and 0.7 cm or between 0.1 cm and 0.3 cm. The protruded brim may protrude from the housing 104. 0.2 cm. The protruded brim 140 may additionally be between 0.1 cm and 0.75 cm or between 0.4 cm and 0.6 cm tall. In some cases, the protruded brim may be 0.5 cm tall. When the protruded brim 140 is mated with the gasket 136 the outer diameter of the assembly may be between 2 cm and 8 cm or between 3 cm and 4.5 cm. In some cases the protruded brim 140 may have an outer diameter of 3.9 cm and an internal diameter of 3.7 cm when mated with the gasket 136.

With continued reference to FIG. 1F-G, gasket 136 may include a gasket opening 144. As used in the current disclosure, a "gasket opening" is an aperture or hole within the gasket. In an embodiment, the body part 128 may be configured to be inserted into the gasket opening 144. This opening aligns the first aperture 136 and the interior of the housing 104 which it is sealing. Thus preventing flow of fluids or gases through the gasket. The size and shape of the gasket opening are configured to match the corresponding elements in the first aperture 136, ensuring a tight and effective seal. In an embodiment, the gasket opening 144 may be between. 5 cm and 1.75 cm or between 0.75 cm and 1.5 cm in diameter. In some cases the gasket opening may be 1.3 cm in diameter.

With continued reference to FIG. 1A, apparatus 100 includes a suction device 148 fluidically connected to the ribbed connector 120 of the end cap 116 using a hose 124. As used in the current disclosure, a "suction device" is a device configured to create a negative pressure environment the housing 104. The suction device 148 may be configured to displace air from inside the housing 104, creating negative pressure. The suction device 148 functions by displacing air from the interior of the housing, effectively reducing the air pressure inside relative to the external environment. This process of air displacement is key to establishing a negative pressure or vacuum within the housing. The specific design of the suction device 148 may include a pump or a motorized mechanism capable of removing air efficiently and maintaining the desired level of negative pressure. Operation of the suction device 148 might be manual or automated.

With continued reference to FIG. 1A, the suction device 148 may consist of a manual pump or a similar hand operated device that creates negative pressure. As used in the current disclosure, a "manual pump" is a mechanical device used to move liquids or gases by manual operation. A manual pump may operate using manual effort to create a pressure differential, thereby moving a fluid or gas. A manual pump may include various components including a piston or plunger, cylinder, inlet valve, outlet valves, one-way valves, handle, and the like. In an embodiment, user may engage a handle/lever using manual force. The handle/lever may be connected to the piston. As the handle is actuated, the piston moves up and down inside the cylinder. When the piston moves upward, it may create a vacuum in the cylinder, causing the inlet valve to open and fluid or gas to be drawn into the cylinder from the housing 104. As the piston is pushed downward, the increased pressure closes the inlet valve and forces the outlet valve open, allowing the fluid or gas to be expelled from the cylinder through the outlet. In an embodiment, both the inlet valve and the outlet valve may be a one-way valves. The one way-valves may be used to prevent the back flow of a gas into the housing 104. This cycle is repeated with each manual operation of the handle or lever, allowing the manual pump to continuously draw in and expel fluid or gas.

With continued reference to FIG. 1A, a suction device 148 may be an automatic suction device. As used in the current disclosure, an "automatic suction device" is a mechanical device that uses electrical energy to move fluids or gases. Unlike manual pumps, an automatic suction device may rely on an electric motor to remove gases from housing 104. The components of an automatic suction device may include an electric motor, an impeller (or other pumping mechanisms), and the like. When the pump is turned on, the electric motor may drive the impeller, creating a centrifugal force or other mechanical action to move the fluid and/or gas. In an embodiment, the automatic suction device may be equipped with a control system to regulate the pressure within the housing. This system can be manually operated or automated, depending on the application. It ensures that the negative pressure is maintained at the desired level.

With continued reference to FIG. 1, an automatic suction device may include a substantially constant pressure pump (e.g., centrifugal pump) or a substantially constant flow pump (e.g., positive displacement pump, gear pump, and the like). Pump can be hydrostatic or hydrodynamic. As used in this disclosure, a "pump" is a mechanical source of power that converts mechanical power into fluidic energy. A pump may generate flow with enough power to overcome pressure induced by a load at a pump outlet. A pump may generate a vacuum at a pump inlet, thereby forcing fluid from a reservoir into the pump inlet to the pump and by mechanical action delivering this fluid to a pump outlet. Hydrostatic pumps are positive displacement pumps. Hydrodynamic pumps can be fixed displacement pumps, in which displacement may not be adjusted, or variable displacement pumps, in which the displacement may be adjusted. Exemplary non-limiting pumps include gear pumps, rotary vane pumps, screw pumps, bent axis pumps, inline axial piston pumps, radial piston pumps, and the like. Pump may be powered by any rotational mechanical work source, for example without limitation and electric motor or a power take off from an engine. Pump may be in fluidic communication with at least a reservoir. In some cases, reservoir may be unpressurized and/or vented. Alternatively, reservoir may be pressurized and/or sealed.

With continued reference to FIG. 1A, apparatus 100 may include a lancet 152 configured to extract bodily fluids from the body part, wherein the lancet is removably attached to the end cap 116. As used in the current disclosure, a "lancet" is medical instrument used to puncture the skin to obtain a sample of bodily fluids. The lancet 152 may have a short, double-edged blade or a needle, which is designed to make a small and shallow cut or puncture. The functional portion of a lancet 152 may be a blade or needle. The tip of the lancet 152 may be very sharp and fine, designed for quick penetration of the skin with minimal pain. In some lancets, the blade is a small, double-edged surgical steel piece, while others use a fine needle. The sharpness and precision of the blade or needle are crucial for ensuring a clean, small puncture that heals quickly. The gauge of the lancet 152 may vary between 28-33 depending on the size of the puncture wound that is desired. Lower gauges are often used when a slightly larger blood sample is needed or for individuals with thicker or calloused skin. Higher gauged lancets 152 may be used for individuals who require frequent blood sampling, such as diabetics who need to monitor their blood sugar levels multiple times a day. In an embodiment, the lancet 152 may be made of stainless steel, while the body may be constructed from medical-grade plastic. The lancet 152 may be removably attached to the housing 104 or the end cap 116. In an embodiment, the end cap 116 may securely hold the lancet in place during the medical procedure. Attachment of the end cap 116 to the lancet 152 may ensure that the lancet can be safely and hygienically transported and stored before use. The lancet 152 may be designed to fit snugly into the end cap 116 using one or more mating connections, such as a push-fit, twist-and-lock, or a Snap-on design. The push-fit mechanism may involve the lancet being pushed into the cap until it clicks into place, indicating a secure fit. In an embodiment, a twist-and-lock mechanism may require the lancet to be inserted and then twisted until it locks into place, ensuring it doesn't accidentally detach. In a snap-on design, the lancet may be pressed into the cap until it snaps into the correct position. In some cases, the lancet 152 may include a covering. The covering might prevent the user from touching the needle directly, reducing the risk of accidental injury or contamination. Some designs allow for the lancet to be re-covered after use for safe disposal, which is important for preventing needle-stick injuries. The end cap also plays a role in maintaining the sterility of the lancet. Until the lancet is used, the cap protects the needle from exposure to contaminants.

With continued reference to FIG. 1A, a lancet 152 may include a spring-loaded lancet. As used in the current disclosure, a "spring-loaded lancet" is a lancet 152 with an integrated spring mechanism. A spring mechanism may be used to control the motion of the lancet needle. When activated, the spring may rapidly propel the lancet forward to puncture the skin and then retract it almost immediately. This quick action helps reduce pain and discomfort. In an embodiment, a spring-loaded lancet may be enclosed within a second housing. The second housing may house the lancet 152 and the spring mechanism. The second housing may be configured to be removably attached to the housing 104 and the end cap 116. In an embodiment, a spring-loaded lancet may include a trigger or button that, when pressed, activates the spring mechanism. The trigger for the lancet 152 may be located on the exterior of the housing 104 or the end cap 116. In an embodiment, a spring-loaded lancet may have an adjustable depth setting. This feature allows the user to control how deeply the lancet penetrates the skin.

With continued reference to FIG. 1A, a lancet 152 may include a laser lancet. As used in the current disclosure, a "laser lancet" is a lancet 152 that employs a focused beam of laser light to make an abrasion on the skin. Unlike traditional mechanical lancets, which use a sharp needle to puncture the skin, a laser lancet utilizes a focused beam of laser light to achieve the same purpose. In an embodiment, a laser lancet may employ a low-powered laser that is precisely focused to create a tiny hole in the skin. The laser may produce a narrow, focused beam of light that can be precisely controlled in terms of wavelength, pulse duration, size and shape of the beam, and intensity. The laser may be calibrated to penetrate only as deep as necessary to reach capillaries for blood sampling, without causing unnecessary damage to the surrounding tissue. The laser makes a clean, precise incision, which typically results in less trauma to the skin as a compared to a traditional lancet. Since the laser lancet does not involve a physical blade or needle penetrating the skin, the risk of infection from the device itself is minimal. This eliminates the need for sterilization procedures required for traditional lancets. An advantage the laser lancet is that it does not require a physical blade or needle penetrating the skin. Because no physical instrument is making contact with the user this greatly reduces the risk of infection. Additionally, eliminates the need for sterilization procedures required for traditional lancets. Laser lancets may require a power source, such as a battery or a connection to the power grid.

With continued reference to FIG. 1A, apparatus 100 may include a fluid collection device 156 configured to collect bodily fluids from the body part 128. As used in the current disclosure, a "fluid collection device" is a specialized apparatus designed for efficiently and hygienically collecting bodily fluids. In some embodiments, the fluid collection device 156 is fluidically connected to the microfluidic assembly. As a non-limiting example, the fluid collection device 156 is configured to collect extracted fluid from the body part. As another non-limiting example, the fluid collection device 156 may be further configured to passively pump the extracted fluid to the microfluidic assembly 200 as described below. In some embodiments, the fluid collection device 156 may include a fluid collection pad. For the purposes of this disclosure, a "fluid collection pad" is a material or device designed to collect and absorb fluids. In some embodiments, the fluid collection pad may include materials that absorb the fluids. As a non-limiting example, the fluid collection pad may include cotton, cellulose, or other absorbent polymers. In some embodiments, the fluid collection device 156 may include a fluid collecting container. As another non-limiting example, the fluid collection device 156 may include a microtiter tube, a dried blood spot, a plasma separating paper, and the like. In some embodiments, the fluid collecting container may include materials that are compatible with the fluids. As a non-limiting example, the fluid collecting container may include plastic, glass, and the like. In some embodiments, the fluid collecting container may include anticoagulants or preservatives to prevent the blood sample from clotting or deteriorating during storage and transportation. In some embodiments, the fluid collection device 156 may be removably inserted into a housing 104 or end cap 116 as described above. The fluid collection device 156 may be removed from the housing 104, the fluid collection device 156 may be inserted into microfluidic assembly 200. In some embodiments, the fluid collection device 156 may be disposable. In some embodiments, the fluid collection device 156 may be replaceable. In some embodiments, the fluid collection device 156 may be used for laboratory-based diagnostic. As a non-limiting example, the fluid collection device 156 may be sent to a laboratory for diagnostic purposes. For example, and without limitation, the fluid collection device 156 may be mailed to the laboratory and analyzed in the laboratory by a trained personnel. In some embodiments, inside the fluid collection device 156, the collected fluid may be separated into different streams going to the different immediate test areas and the different storage techniques. In some embodiments, the collected fluid may be either diluted, undiluted or lysed.

With continued reference to FIGS. 1A-C, the end cap 116 may include an adjustable height feature 160. As used in the current disclosure, an "adjustable height feature" is a mechanism that allows a user to adjust the height of the interior portion of the end cap 116. This may include raising or lowering the interior portion of the end cap 116 that is exposed within the housing 104. The adjustable height feature 160 may allow the housing 104 and the end cap 116 to accommodate body parts of various sizes and shapes. Additionally, the adjustable height feature 160 may allow the end cap 116 to accommodate various sizes or types of attachments (like lancets 152 or fluid collection devices 156) or to control the depth of penetration in procedures like blood sampling. In an embodiment, end cap 116 could be designed with a threaded mechanism, allowing it to be screwed up or down to adjust the height. For example, turning the end cap 116 in one direction may extend the interior of the end cap downward thus reducing the interior height of the mated housing 104 and end cap 116. Alternatively, turning the end cap 116 in the opposite direction may retract the interior of the end cap thus increasing the interior height of the mated housing 104 and end cap 116. This approach to the adjustable height feature 160 may require that a portion of the interior of the housing be threaded. The threaded portion of the housing 104 may be mated with a threaded portion of the end cap 116. This may allow then end cap 116 to be selectively extended or retracted. In an embodiment, an adjustable height feature 160 may be configured to be in an extended position or a retracted position. An extended position may be a position where the adjustable height feature 160 is extended to allow the lancet 152 and/or the fluid collection device 156 to encounter the body part. A retracted position may be a position where the adjustable height feature 160 has not been extended or adjusted. In another non-limiting example, the adjustable height feature 160 may include a telescoping feature. One or more portions of the interior of the end cap 116 may be configured to extend downward in a telescopic manner, where segments of the end cap slide over each other to increase or decrease the height. This may result in a tiered appearance of the interior of the end cap. In an embodiment, the adjustable height feature 160 may include a locking mechanism. The locking mechanism may be configured to have at least two positions, engaged, and disengaged. When the locking mechanism is in the engaged position, the adjustable height feature 160 may securely hold end cap 116 in the chosen height position, preventing accidental retraction or extension during use. Alternatively, when the locking mechanism is in the disengaged position the adjustable height feature 160 may be freely used to adjust the height of the end cap.

With continued reference to FIGS. 1A-G, apparatus 100 may be used to extract bodily fluids from a body part during a fluid extraction process. As used in the current disclosure, a "fluid extraction process" is a process that applies controlled pressure to encourage the flow of bodily fluid from the puncture site. Bodily fluid may be any fluid that is within the body including blood, pus, foreign fluids, venom, poison, inflammatory fluids, and the like. This process can be particularly useful in scenarios where passive blood flow is insufficient. The fluid extraction process may include sterilizing the body part where blood will be drawn. During the fluid extraction process the body part may be inserted into the housing 104. The body part may be configured to mate with the housing 104 and the gasket 136 to form an airtight seal. This airtight seal may be created by compressing the gasket 136 using the body part. The compression of the gasket removes all gaps between the body part and the housing 104 thus creating the airtight seal. While compressing the gasket 136, the body part may be configured to extend into the housing 104 so that it is in range of the fluid collection device 156 and the lancet 152. The adjustable height feature of the end cap 116 may be used to modify the height of the lancet 152 and the fluid collection device 156 within the housing. This may be done to accommodate body parts of varying sizes. Once the body part is within range, a user may then activate the suction device 148. The suction device 148 may be used to create a negative pressure environment within the sealed housing. The negative pressure within the housing 104 applies pressure to the body part and encourages the bodily fluids of the user to come to the surface. Once adequate pressure is applied, the skin of the user may be punctured using the lancet 152 to access a capillary or small blood vessel. The negative pressure environment may help in pushing the bodily fluids out through this puncture. As the bodily fluids emerge from the puncture site, it is collected into a fluid collection device 156. The positive pressure may aid in providing a sufficient quantity of blood for the test or analysis required.

Figure 2:
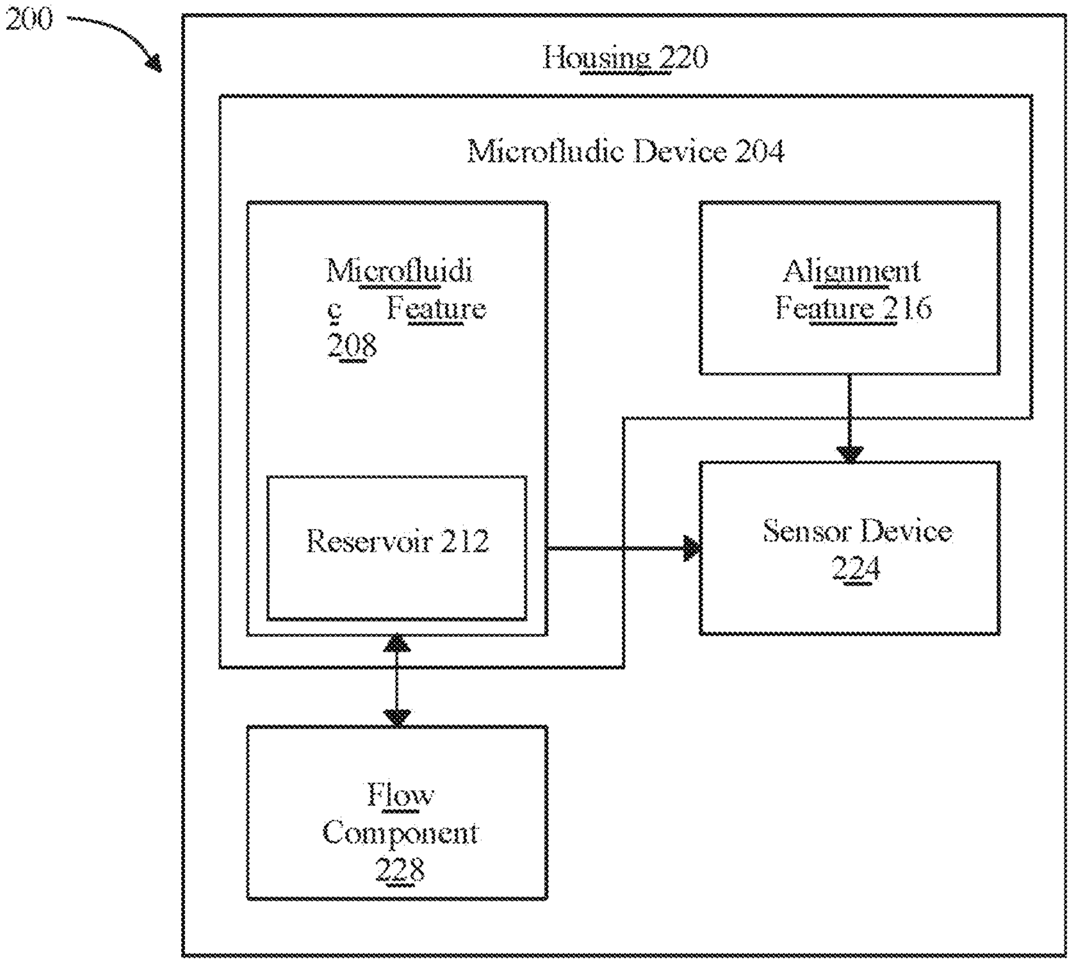
FIG. 2 is an exemplary embodiment of an apparatus for performing microfluidic-based biochemical assay.

Referring now to FIG. 2, an exemplary embodiment of an apparatus 200 for performing microfluidic-based biochemical assays is illustrated. As used in this disclosure, a "microfluidic-based biochemical assay" is an assay on small volumes (i.e., in unit of ml or nl) of fluids. In some embodiments, microfluidic-based biochemical assay may be used for a wide range of applications, such as without limitation, medical diagnostics, drug discovery, environmental monitoring, and food safety testing, and the like. Apparatus 200 may include a computing device. Computing device may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device may include a single computing device operating independently, or may include two or more computing device operating in concert, in parallel, sequentially or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device may include but is not limited to, for example, a computing device or cluster of computing devices in a first location and a second computing device or cluster of computing devices in a second location. Computing device may include one or more computing devices dedicated to data storage, security, distribution of traffic for load balancing, and the like. Computing device may distribute one or more computing tasks as described below across a plurality of computing devices of computing device, which may operate in parallel, in series, redundantly, or in any other manner used for distribution of tasks or memory between computing devices. Computing device may be implemented using a "shared nothing" architecture in which data is cached at the worker, in an embodiment, this may enable scalability of apparatus 200 and/or computing device.

With continued reference to FIG. 2, computing device may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 2, apparatus 200 includes a microfluidic device 204. As used in this disclosure, a "microfluidic device" is a device that is configured to act upon fluids at a small scale, such as without limitation a sub-millimeter scale. At small scales, surface forces may dominate volumetric forces. In a non-limiting example, microfluidic device may be consistent with any microfluidic device described in U.S. patent application Ser. No. 17/859,932, filed on Jul. 7, 2022, entitled "SYSTEM AND METHODS FOR FLUID SENSING USING PASSIVE FLOW," the entirety of which is incorporated herein by reference. In an additional non-limiting example, microfluidic device may be consistent with any microfluidic device described in U.S. patent application Ser. No. 18/199,199, filed on May 18, 2023, entitled "APPARATUS AND METHODS FOR PERFORMING MICROFLUIDIC-BASED BIOCHEMICAL ASSAYS," the entirety of which is incorporated herein by reference.

With continued reference to FIG. 2, microfluidic device 204 includes at least a microfluidic feature 208. As used in this disclosure, a "microfluidic feature" is a structure within microfluidic device 204 that is designed and/or configured to manipulate one or more fluids at micro scale. In a non-limiting example, microfluidic feature 208 may include, without limitation, reservoir, microfluidic channel, conjugate pad, and the like as described in further detail below in this disclosure. In some cases, microfluidic feature 208 may enable a precise manipulation of fluids and samples in a controlled and/or reproducible manner within microfluidic device 204. In some embodiments, microfluidic feature 208 of microfluidic device 204 may be designed and arranged based on particular needs of a given microfluidic-based biochemical assay. In other embodiments, microfluidic feature 208 of microfluidic device 204 may be varied depending on the type of the at least a fluid being used, that is directly contact with microfluidic feature 208. In a non-limiting example, attributes of microfluidic feature 208 such as, without the size and/or shape of the substrate may be determined as a function of specific assay protocols. Exemplary embodiments of microfluidic feature 208 are described in further detail below in this disclosure.

With continued reference to FIG. 2, microfluidic feature 208 includes at least a reservoir 212. Reservoir 212 may be configured to contain at least a fluid. In a non-limiting example, fluid may include a sample fluid to be analyzed from a subject; for instance, and without limitation, reservoir 212 of microfluidic device 204 may contain a blood sample taken from a patient. In an embodiment, reservoir 212 may be removably attached to microfluidic device 204. This removable attachment may allow the reservoir 212 to be disposable after a single use. Additionally, fluid may include one or more suspensions and/or solutions of reagents, molecules, or other items to be analyzed and/or utilized, including without limitation monomers such as individual nucleotides, amino acids, or the like, one or more buffer solutions and/or saline solutions for rinsing steps, and/or one or more analytes to be detected and/or analyzed. Fluid and/or microfluidic device may be used, without limitation, in processes as disclosed in U.S. Nonprovisional application Ser. No. 17/337,931, filed on Jun. 3, 2021, and entitled "METHODS AND SYSTEMS FOR MONOMER CHAIN FORMATION," and/or as disclosed in U.S. Nonprovisional application Ser. No. 17/403,480, filed on Aug. 16, 2021, and entitled "TAGGED-BASE DNA SEQUENCING READOUT ON WAVEGUIDE SURFACES," the entirety of each of which is incorporated herein by reference. Reservoir 212 may have at least an inlet, at least an outlet, or both. Reservoir 212 may further include, without limitation, a well, a channel, a flow path, a flow cell, a pump, and the like. In a non-limiting example, fluid may be input through the at least an inlet into reservoir 212 and/or output through the at least an outlet. At least an outlet may be connected to other components and/or devices within microfluidic device 204; for instance, and without limitation, at least an outlet may be connected to other microfluidic feature 208 such as microfluidic channel as described below in this disclosure.

With continued reference to FIG. 2, reservoir 212 may be configured to fluidically connected with a fluid collection device 156. In an embodiment, a fluid collection device 156 may be configured to be fluidically connected to reservoir 212, enabling the transfer of fluids between these two components. In one embodiment, the fluid collection device 156 can be detachably connected to the end cap 116 and is also designed to be fluidically connected to the reservoir 212. This embodiment may allow for the bodily fluids collected in the fluid collection device 156 to be easily transferred into the reservoir 212, potentially through a connecting hose or tubing that ensures a fluid path between them. In an additional embodiment, reservoir 212 may be the same or substantially similar to fluid collection device 156. This interchangeability means that the fluid collection device 156, once removed from the assembly 100, can directly function as the reservoir 212 when mated with a microfluidic device 204. The process may involve inserting the fluid collection device 156 into an alignment feature of the microfluidic device 204, ensuring proper positioning and functionality. This dual functionality of the fluid collection device 156 as both a collector and a reservoir 212 may be done to maximize the sample provided by user in the most sterile manner possible.

With continued reference to FIG. 2, microfluidic device 204 includes at least an alignment feature 216 at a distance from at least a microfluidic feature 208. In a microfluidic device used for performing biochemical assays, an "alignment feature" is a physical feature that helps to precisely align components of microfluidic device 204 with other components. Alignment features 216 is configured for precise positioning and attaching of a fluid collection device 156, reservoir 212, or a sensor device, wherein the sensor device may include any sensor device as described in this disclosure. In an embodiment, an alignment feature 216 may be configured to facilitate a fluidic communication between the microfluidic device 204 and the reservoir 212. In some embodiments, alignment feature 216 may be configured for precise positioning and attaching other components external to apparatus 200; for instance, and without limitation, without limitation, an external device may be coupled with apparatus 200 through one or more alignment features 216, such as, without limitation, a multi-fiber push connector (MPO), bracket, press fastener (with spring mechanism) or the like as described in further detail below. In some embodiments, alignment feature 216 may be configured for precise positioning microfluidic feature 208; for instance, and without limitation, microfluidic channel may be etched along alignment feature 216 during etching process as described below. In some cases, microfluidic channel may be configured to be in parallel to alignment feature 216 at a distance. In other cases, microfluidic channel may be configured to be perpendicular to alignment feature 216 at a distance. Other embodiments of microfluidic feature 208 alignment employing alignment feature 216 as reference may include, without limitation, symmetrical alignment, relative positioning, fix positioning, and the like thereof.

With continued reference to FIG. 2, in some embodiments, alignment feature 216 may include a housing 220. As used in this disclosure, a "housing" refers to an outer structure configured to contain a plurality of components, such as, without limitation, components of apparatus 200 as described in this disclosure. In a non-limiting example, alignment feature 216 may include an outer casing of apparatus 200. In some cases, housing 220 may be made from a durable, lightweight material such as without limitation, plastic, metal, and/or the like. In some embodiments, housing 220 may be designed and configured to protect sensitive components of apparatus 200 from damage or contamination. In a non-limiting example, at least an alignment feature 216 may include one or more flat facets located on housing 220 configured to constraint at least a sensor device as described above in this disclosure, wherein the "flat facet" refers to a surface or object that is smooth and event, without any significant curvature or bumps. In another non-limiting example, at least an alignment feature 216 may include one or more physical notches and/or grooves that allow for precise placement of devices and/or components. In yet another non-limiting example, at least an alignment feature 216 may include one or more optical markers or alignment indicators that are visible (through human eye, microscope, any other imaging system, and/or the like) and allow for accurate positioning of devices and/or components. In a further non-limiting examples, at least an alignment feature 216 may include one or more tapered or angled surfaces (of housing 220) that guide the one or more microfluidic features 208 through apparatus 200. In other non-limiting example, housing 220 may include one or more surface coatings and/or modifications that reduce the likelihood of unwanted adhesion or interference with external components such as, without limitation, external device as described in further detail below. Additionally, or alternatively, at least an alignment feature 216 may further include features such as latches, clips, or other fasteners that help to secure apparatus 200 in place during use. In an embodiment, housing 220 may be incorporated into interior portion of the end cap 116 or housing 104 of apparatus 100.

Still referring to FIG. 2, in some embodiments, at least an alignment feature 216 may include a sealer. As used in this disclosure, a "sealer" is a component that is used to create a secure seal between components of apparatus 200. In some cases, sealer may be configured to prevent contamination (i.e., dust, debris, other external factors, and/or the like) of the fluids, thus ensuring accurate, reliable results. In a non-limiting example, sealer of at least an alignment feature 216 may be configured to seal between one or more microfluidic features 208 within microfluidic device 204 and housing 220. In some embodiments, sealers can take many forms, depending on the overall design and/or configuration of apparatus 200; for instance, and without limitation, sealer may include O-rings, gaskets, adhesives, or other materials that are used to fill gaps and/or create a fluid-tight seal between microfluidic channel and housing 220. In some embodiments, sealer may be applied to the surface of microfluidic device 204 to create a barrier between microfluidic feature 208 with external environment. In some cases, sealer may be heat-scalable. In a non-limiting example, sealer may include a heat-scalable film or tape, made from a flexible, thermoplastic material that can be heated and molded to the contours of the apparatus 200, creating a barrier between the microfluidic device 204 and the external environment.

With continued reference to FIG. 2, apparatus 200 includes a sensor device 224. Sensor device 224 may be configured to be in sensed communication with at least a fluid contained within or otherwise acted upon by microfluidic feature 208. As used in this disclosure, a "sensor device" is one or more independent sensors, as described herein, where any number of the described sensors may be used to detect any number of physical quantities associated with a microfluidic environment. In some embodiments, sensor device 224 may include an optical device. As used in this disclosure, an "optical device" is any device that generates, transmits, detects, or otherwise functions using electromagnetic radiation, including without limitation ultra-violet light, visible light, near infrared light, infrared light, and the like. In some embodiments, optical device may include one or more waveguide. As used in this disclosure, a "waveguide" is a component that is configured to propagate electromagnetic radiation, including without limitation ultra-violet light, visible light, near infrared light, infrared light, and the like. A waveguide may include a lightguide, a fiberoptic, or the like. A waveguide may include a grating within a transmissive material. In some cases, a waveguide may be configured to function as one or more optical devices, for example a resonator (e.g., micro resonator), an interferometer, or the like. In some cases, waveguide may be configured to propagate an electromagnetic radiation (EMR). In a non-limiting example, sensor device 224 may include any sensor device described in U.S. patent application Ser. No. 17/859,932 and/or any other disclosure incorporate by reference herein. Sensor device 224 may include a sensor, wherein the sensor may be optical communication with one or more waveguide. Such sensor may be configured to detect a variance in at least an optical property associated with the at least a fluid. As used in this disclosure, an "optical property" is any detectable characteristic associated with electromagnetic radiation, for instance UV, visible light, infrared, and the like. In some cases, sensor device may generate and/or communicate signal representative of the detected property.

Still referring to FIG. 2, in some embodiments, sensor may be in communication with the computing device. For instance, and without limitation, sensor 228 may communicate with computing device using one or more signals. As used in this disclosure, a "signal" is a human-intelligible and/or machine-readable representation of data, for example and without limitation an electrical and/or digital signal from one device to another; signals may be passed using any suitable communicative connection. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure. A signal may include an optical signal, a hydraulic signal, a pneumatic signal, a mechanical signal, an electric signal, a digital signal, an analog signal, and the like. In some cases, a signal may be used to communicate with a computing device, for example by way of one or more ports. In some cases, a signal may be transmitted and/or received by computing device, for example by way of an input/output port. An analog signal may be digitized, for example by way of an analog to digital converter. In some cases, an analog signal may be processed, for example by way of any analog signal processing steps described in this disclosure, prior to digitization. In some cases, a digital signal may be used to communicate between two or more devices, including without limitation computing devices. In some cases, a digital signal may be communicated by way of one or more communication protocols, including without limitation internet protocol (IP), controller area network (CAN) protocols, serial communication protocols (e.g., universal asynchronous receiver-transmitter [UART]), parallel communication protocols (e.g., IEEE 128 [printer port]), and the like.

Still referring to FIG. 2, in some cases, apparatus 200, sensor, and/or computing device may perform one or more signal processing steps on a signal. For instance, apparatus 200, sensor, and/or computing device may analyze, modify, and/or synthesize a signal representative of data in order to improve the signal, for instance by improving transmission, storage efficiency, or signal to noise ratio. Exemplary methods of signal processing may include analog, continuous time, discrete, digital, nonlinear, and statistical. Analog signal processing may be performed on non-digitized or analog signals. Exemplary analog processes may include passive filters, active filters, additive mixers, integrators, delay lines, compandors, multipliers, voltage-controlled filters, voltage-controlled oscillators, phase-locked loops, and/or any other process using operational amplifiers or other analog circuit elements. Continuous-time signal processing may be used, in some cases, to process signals which vary continuously within a domain, for instance time. Exemplary non-limiting continuous time processes may include time domain processing, frequency domain processing (Fourier transform), and complex frequency domain processing. Discrete time signal processing may be used when a signal is sampled non-continuously or at discrete time intervals (i.e., quantized in time). Analog discrete-time signal processing may process a signal using the following exemplary circuits sample and hold circuits, analog time-division multiplexers, analog delay lines and analog feedback shift registers. Digital signal processing may be used to process digitized discrete-time sampled signals. Commonly, digital signal processing may be performed by a computing device or other specialized digital circuits, such as without limitation an application specific integrated circuit (ASIC), a field-programmable gate array (FPGA), or a specialized digital signal processor (DSP). Digital signal processing may be used to perform any combination of typical arithmetical operations, including fixed-point and floating-point, real-valued, and complex-valued, multiplication and addition. Digital signal processing may additionally operate circular buffers and lookup tables. Further non-limiting examples of algorithms that may be performed according to digital signal processing techniques include fast Fourier transform (FFT), finite impulse response (FIR) filter, infinite impulse response (IIR) filter, and adaptive filters such as the Wiener and Kalman filters. Statistical signal processing may be used to process a signal as a random function (i.e., a stochastic process), utilizing statistical properties. For instance, in some embodiments, a signal may be modeled with a probability distribution indicating noise, which then may be used to reduce noise in a processed signal.

With continued reference to FIG. 2, in some embodiments, apparatus 200 may include one or more light sources. As used in this disclosure, a "light source" is any device configured to emit electromagnetic radiation, such as without limitation light, UV, visible light, and/or infrared light. In some cases, a light source may include a coherent light source, which is configured to emit coherent light, for example a laser. In some cases, a light source may include a non-coherent light source configured to emit non-coherent light, for example a light emitting diode (LED). In some cases, light source may emit a light having substantially one wavelength. In some cases, light source may emit a light having a wavelength range. Light may have a wavelength in an ultraviolet range, a visible range, a near-infrared range, a mid-infrared range, and/or a far-infrared range. For example, in some cases light may have a wavelength within a range from about 200 nm to about 20 micrometers. In some cases, light may have a wavelength within a range of about 400 nm to about 2,500 nm. Light sources may include, one or more diode lasers, which may be fabricated, without limitation, as an element of an integrated circuit; diode lasers may include, without limitation, a Fabry Perot cavity laser, which may have multiple modes permitting outputting light of multiple wavelengths, a quantum dot and/or quantum well-based Fabry Perot cavity laser, an external cavity laser, a mode-locked laser such as a gain-absorber system, configured to output light of multiple wavelengths, a distributed feedback (DFB) laser, a distributed Bragg reflector (DBR) laser, an optical frequency comb, and/or a vertical cavity surface emitting laser. Light source may additionally or alternatively include a light-emitting diode (LED), an organic LED (OLED) and/or any other light emitter. In some cases, light source may be configured to couple light into optical device, for instance into one or more waveguide described above.

With continued reference to FIG. 2, in some embodiments, at least a sensor device 224 may include at least a photodetector. In some cases, at least a sensor device 224 may include a plurality of photodetectors, for instance at least a first photodetector and at least a second photodetector. In some cases, at least a first photodetector and/or at least a second photodetector may be configured to measure one or more of first optical output and second optical output, from a first waveguide and a second waveguide, respectively. As used in this disclosure, a "photodetector" is any device that is sensitive to light and thereby able to detect light. In some cases, a photodetector may include a photodiode, a photoresistor, a photosensor, a photovoltaic chip, and the like. In some cases, photodetector may include a Germanium-based photodiode. Light detectors may include, without limitation, Avalanche Photodiodes (APDs), Single Photon Avalanche Diodes (SPADs), Silicon Photomultipliers (SiPMs), Photo-Multiplier Tubes (PMTs), Micro-Channel Plates (MCPs), Micro-Channel Plate Photomultiplier Tubes (MCP-PMTs), Indium gallium arsenide semiconductors (InGaAs), photodiodes, and/or photosensitive or photon-detecting circuit elements, semiconductors and/or transducers. Avalanche Photo Diodes (APDs), as used herein, are diodes (e.g., without limitation p-n, p-i-n, and others) reverse biased such that a single photon generated carrier can trigger a short, temporary "avalanche" of photocurrent on the order of milliamps or more caused by electrons being accelerated through a high field region of the diode and impact ionizing covalent bonds in the bulk material, these in turn triggering greater impact ionization of electron-hole pairs. APDs provide a built-in stage of gain through avalanche multiplication. When the reverse bias is less than the breakdown voltage, the gain of the APD is approximately linear. For silicon APDs this gain is on the order of 10-100. Material of APD may contribute to gains. Germanium APDs may detect infrared out to a wavelength of 1.7 micrometers. InGaAs may detect infrared out to a wavelength of 1.6 micrometers. Mercury Cadmium Telluride (HgCdTe) may detect infrared out to a wavelength of 14 micrometers. An APD reverse biased significantly above the breakdown voltage is referred to as a Single Photon Avalanche Diode, or SPAD. In this case the n-p electric field is sufficiently high to sustain an avalanche of current with a single photon, hence referred to as "Geiger mode." This avalanche current rises rapidly (sub-nanosecond), such that detection of the avalanche current can be used to approximate the arrival time of the incident photon. The SPAD may be pulled below breakdown voltage once triggered in order to reset or quench the avalanche current before another photon may be detected, as while the avalanche current is active carriers from additional photons may have a negligible effect on the current in the diode. At least a first photodetector may be configured to generate a first signal as a function of variance of an optical property of the first waveguide, where the first signal may include without limitation any voltage and/or current waveform. Additionally, or alternatively, sensor device may include a second photodetector located down beam from a second waveguide. In some embodiments, second photodetector may be configured to measure a variance of an optical property of second waveguide and generate a second signal as a function of the variance of the optical property of the second waveguide.

With continued reference to FIG. 2, in some cases, photodetector may include a photosensor array, for example without limitation a one-dimensional array. Photosensor array may be configured to detect a variance in an optical property of waveguide. In some cases, first photodetector and/or second photodetector may be wavelength dependent. For instance, and without limitation, first photodetector and/or second photodetector may have a narrow range of wavelengths to which each of first photodetector and second photodetector are sensitive. As a further non-limiting example, each of first photodetector and second photodetector may be preceded by wavelength-specific optical filters such as bandpass filters and/or filter sets, or the like; in any case, a splitter may divide output from optical matrix multiplier as described below and provide it to each of first photodetector and second photodetector. Alternatively, or additionally, one or more optical elements may divide output from waveguide prior to provision to each of first photodetector and second photodetector, such that each of first photodetector and second photodetector receives a distinct wavelength and/or set of wavelengths. For example, and without limitation, in some cases a wavelength demultiplexer may be disposed between waveguides and first photodetector and/or second photodetector; and the wavelength demultiplexer may be configured to separate one or more lights or light arrays dependent upon wavelength. As used in this disclosure, a "wavelength demultiplexer" is a device that is configured to separate two or more wavelengths of light from a shared optical path. In some cases, a wavelength demultiplexer may include at least a dichroic beam splitter. In some cases, a wavelength demultiplexer may include one of a hot mirror, a cold mirror, a short-pass filter, a long pass filter, a notch filter, and the like. An exemplary wavelength demultiplexer may include part No. WDM-11P from OZ Optics of Ottawa, Ontario, Canada. Further examples of demultiplexers may include, without limitation, gratings, prisms, and/or any other devices and/or components for separating light by wavelengths that may occur to persons skilled in the art upon reviewing the entirety of this disclosure. In some cases, at least a photodetector may be communicative with computing device, such that a sensed signal may be communicated with computing device.

With continued reference to FIG. 2, in some embodiments, microfluidic feature 208 may include a sensor interface. Sensor interface may be configured to wet waveguide with at least a fluid contained within or otherwise acted upon by microfluidic device 204. As used in this disclosure, a "sensor interface" is an arrangement permits sensor device 224 to be in sensed communication with microfluidic device 204. In some embodiments, sensor interface may include an optical interface. As used in this disclosure, an "optical interface" is an arrangement permits optical device to be in sensed communication with microfluidic device 204. In one embodiment, sensor device may be coupled to a sensor interface that includes a porous membrane (e.g., nitrocellulose, paper, glass fiber, etc.) as described below that promotes capillary flow. In some cases, a surface of sensor device may be modified with hydrophilic chemistry, for instance by way of silanes, proteins, or another treatment (or may already be hydrophilic) in the sensing region. For example, one or more sensor devices and sensor interfaces may be configured such that liquid wicks from a porous membrane to a surface of sensor device as it flows through the membrane.

Still referring to FIG. 2, in some embodiments, sensor interface of microfluidic feature 208 may include a flow cell. As used in this disclosure, a "flow cell" is a component of or associated with a microfluidic device that contains and provides access to a fluid or a flow of a fluid for a sensor interface arrangement. In some cases, a flow cell may effectively increase an area over which at least a fluid flows, thereby increasing access to the at least a fluid for optical sensing. In some cases, a flow cell may include micro-posts. In some cases, a flow cell may include a plurality of micro-posts. As used in this disclosure, "micro-posts" are small scale (e.g., sub-millimeter) protrusions which break up a flow path. In some cases, a micro-post property may be varied in order to affect a flow property. Exemplary non-limiting micro-post properties include pitch, micro-post width (e.g., diameter), micro-post arrangement (e.g., hexagonal), micro-post size (e.g., column), micro-post height, number of micro-posts (total, in a row, in a column, etc.), and the like.

Still referring to FIG. 2, in some embodiments, sensor interface of microfluidic feature 208 may include a porous membrane. As used in this disclosure, a "porous membrane" is a material with a plurality of voids. In some cases, a porous membrane may have at least a membrane property selected to achieve at least a flow property. As used in this disclosure, a "membrane property" is an objective characteristic associated with a porous membrane. Exemplary non-limiting membrane properties include pore size, porosity, measures of hydrophilicity, measures of surface tension, measures of capillary action, material, and the like. In some embodiments, a porous membrane interfacing with at least a sensor device 224 and microfluidic device 204 and/or microfluidic feature 208 may provide several advantages. In a non-limiting example, a porous membrane connecting two segments of a channel may provide fluidic communication, connecting one segment of the channel to another; (the porous membrane may, thus, carry reagents and/or samples in solution, and open the channel to an outside environment while maintaining fluidic flow to the microfluidic device 204 and/or microfluidic feature 208). In another non-limiting example, a porous membrane may eliminate need for a gasket (which may leak and result in poor yield). In a further non-limiting example, a porous membrane may help control one or more flow properties. As used in this disclosure, "flow properties" are characteristics related to a flow of a fluid as described in further detail below in this disclosure. For instance, exemplary non-limiting flow properties include flow rate (in μl/min), flow velocity, integrated flow volume, pressure, differential pressure, and the like. For instance, and without limitation, flow rate within microfluidic feature 208 may be determined by pore size, pore density, membrane material, and porous membrane dimensions. In other non-limiting examples, a porous membrane strip interfacing at least a sensor device 224 to microfluidic device 204 and/or microfluidic feature 208 may require less precision.

With continued reference to FIG. 2, in some embodiments, microfluidic feature 208 may include at least a channel. As used in this disclosure, a "channel" is a reservoir having one or more of an inlet (i.e., input) and an outlet (i.e., output). Channels may have a sub millimeter scale consistent with microfluidics. Channels may have channel properties which affect other system properties (e.g., flow properties, flow timing, and the like). As used in this disclosure, "flow timing" is any time-dependent property associated with a flow of at least a fluid. For instance, in some cases, flow timing may include a duration for a flow to reach, pass through, or otherwise interact with an element of microfluidic device 204 and/or other microfluidic features; for instance, and without limitation, flow out from reservoir 212. As used in this disclosure, "channel properties" are objective characteristics associated with channels or a microfluidic device generally. Exemplary non-limiting channel properties include width, height, length, material, surface roughness, cross-sectional area, layout, and the like. Additionally, or alternatively, microfluidic feature 208 may include a microfluidic circuit. As used in this disclosure, a "microfluidic circuit" is a configuration of a plurality of microscale fluidic components within microfluidic device 204. Microscale fluidic components may include any microfluidic feature 208 of microfluidic device 204 as described above. In a non-limiting example, microfluidic circuit may include a configuration of channels, individually addressable valves, and chambers through which fluid is allowed to flow. Microfluidic circuit disclosed here may be consistent with any microfluidic circuit described in U.S. patent application Ser. No. 18/107,135, filed on Feb. 8, 2023, entitled "APPARATUS AND METHODS FOR ACTUATING FLUIDS IN A BIOSENSOR CARTRIDGE," the entirety of which is incorporated herein by reference.

With continued reference to FIG. 2, microfluidic device 204 with integrated sensor device 224 may be utilized in an advanced diagnostic device or diagnostic sensor for detection of biological signatures (e.g., viruses, bacteria, pathogens, and the like). In some cases, microfluidic feature 208 may be fabricated on a substrate. Substrate may be composed of various materials, such as glass, silicon, and the like. In one or more embodiments, microfluidic device 204 containing microfluidic features may be fabricated using various processes, such as, for example, photolithography, injection molding, stamping processes, and the like. In various embodiments, substrate may be substantially planar. In some embodiments, microfluidic feature 208 may be built on a substrate using, for example, photosensitive polymers or photoresists (e.g., SU-8, Ostemer, and the like). In other embodiments, microfluidic feature 208 may be molded or stamped into polymers (e.g., PMMA). In other embodiments, components and/or devices of microfluidic device 204 may be built into or on substrate using etching processes, in which channels, reservoir 212, capillary pumps, and valves may be built by removing materials from substrate. In non-limiting embodiments, the entire microfluidic system may be fabricated on substrate, sealed with a cover plate, where holes are drilled and aligned with certain microfluidic components, such as reservoir 212. Additionally, or alternatively, substrate may then be diced into small chips. Chips may also be fabricated with microfluidic features etch or patterned on them. Further, they can be coupled to microfluidic features fabricated separately on another substrate such as plastic or glass.

With continued reference to FIG. 2, apparatus 200 further includes at least a flow component 228 connected with at least a microfluidic feature 208 configured to flow at least a fluid through at least a sensor device 224. In some embodiments, at least a flow component 228 may include a passive flow component configured to initiate a passive flow process. As used in this disclosure, a "passive flow component" is a component, typically of a microfluidic device, that imparts a passive flow on a fluid, wherein the "passive flow," for the purpose of this disclosure, is flow of fluid, which is induced absent any external actuators, fields, or power sources. As used in this disclosure, a "passive flow process" is a plurality of actions or steps taken on passive flow component in order to impart a passive flow on at least a fluid. Passive flow component may employ one or more passive flow techniques in order to initiate passive flow process; for instance, and without limitation, passive flow techniques may include osmosis, capillary action, surface tension, pressure, gravity-driven flow, hydrostatic flow, vacuums, and the like. Passive flow component may be in fluidic communication with at least a reservoir 212. Exemplary non-limiting passive flow component is explained in greater detail in this disclosure below. Passive flow component may be configured to flow at least a fluid stored in at least a reservoir 212 with predetermined flow properties. In a non-limiting example, passive flow component may be consistent with any passive flow component described in U.S. patent application Ser. No. 17/859,932, filed on Jul. 7, 2022, entitled "SYSTEM AND METHODS FOR FLUID SENSING USING PASSIVE FLOW," the entirety of which is incorporated herein by reference.

With continued reference to FIG. 2, in other embodiments, at least a flow component 228 may include an active flow component configured to initiate an active flow process. As used in this disclosure, an "active flow component" is a component that imparts an active flow on a fluid, wherein the "active flow," for the purpose of this disclosure, is flow of fluid which is induced by external actuators, fields, or power sources. As used in this disclosure, an "active flow process" is a plurality of actions or steps taken on active flow component in order to impart active flow on at least a fluid. In some embodiments, active flow component 216 is in fluidic communication with at least a reservoir 212. In a non-limiting example, active flow component may include one or more pumps. Pump may include a substantially constant pressure pump (e.g., centrifugal pump) or a substantially constant flow pump (e.g., positive displacement pump, gear pump, and the like). Pump can be hydrostatic or hydrodynamic. As used in this disclosure, a "pump" is a mechanical source of power that converts mechanical power into fluidic energy. A pump may generate flow with enough power to overcome pressure induced by a load at a pump outlet. A pump may generate a vacuum at a pump inlet, thereby forcing fluid from a reservoir into the pump inlet to the pump and by mechanical action delivering this fluid to a pump outlet. Hydrostatic pumps are positive displacement pumps. Hydrodynamic pumps can be fixed displacement pumps, in which displacement may not be adjusted, or variable displacement pumps, in which the displacement may be adjusted. Exemplary non-limiting pumps include gear pumps, rotary vane pumps, screw pumps, bent axis pumps, inline axial piston pumps, radial piston pumps, and the like. Pump may be powered by any rotational mechanical work source, for example without limitation and electric motor or a power take off from an engine. Pump may be in fluidic communication with at least a reservoir 212. In some cases, reservoir 212 may be unpressurized and/or vented. Alternatively, reservoir 212 may be pressurized and/or scaled; for instance, by alignment component 216 such as, without limitation, sealer as described above. In a non-limiting example, active flow component may include any active flow component as described in U.S. patent application Ser. No. 18/107,135.

With continued reference to FIG. 2, in some cases, development of microfluid feature layout, selection of flow component, and sensor interface may need to be performed in an iterative design process as each parameter is interdependent with important system properties (e.g., flow properties and flow timing). In some embodiments, aspect ratios of chambers (e.g., reservoir 212), fluidic resistances (controlled by dimensions) of channels between the chambers (and sensor interface), and flow component parameters (e.g., pump pressure) may be tuned to affect one or both of timing and flow of at least a fluid. In some embodiments, microfluidic feature 208 within microfluidic device 204 of apparatus 200 may be hydrophilic, for example through coating, to ensure flow. Alternatively, or additionally, microfluidic device 204 may include a hydrophilic material, such as without limitation polymethyl methacrylate (PPMA). Further, a reagent chamber may be placed such that the sensor reaction chamber is between the reagent chamber and the sample chamber.

With continued reference to FIG. 2, At least a sensor device 224 may be disposed in a sensor area. As used in this disclosure, a "sensor area" is a position, a location, or otherwise an area determined by at least an alignment feature 216 as described above. In some embodiments, sensor area may match with at least a surface of sensor device 224; for instance, and without limitation, alignment feature 216 may include a slightly depressed plane, wherein the slightly depressed plane may include a same surface area with the at least a surface of sensor device 224. In some embodiments, microfluidic feature 208 may be configured to pass through sensor area. In some cases, microfluidic feature 208 such as microfluidic channels may pass underneath sensor area 204. In other cases, microfluidic feature 208 such as microfluidic channels may pass above sensor area 204. In a non-limiting example, sensor area may be located at a first layer, wherein the first layer may be above or below a second layer containing the microfluidic environment. At least an alignment feature 216, such as, without limitation, a sealer, may be placed between the first layer and the second layer; however, the sealer may avoid at least a portion of sensor area 204 in order for sensor device 224 disposed at sensor area to detect sensed properties as described above, such as, without limitation, optical properties (e.g., wavelength, frequency, intensity, polarization, spectral distribution, absorption and emission spectra, and the like) and flow properties (e.g., flow rate, flow velocity, integrated flow volume, pressure, and the like). As used in this disclosure, a "microfluidic environment" refers to a complex system of plurality of microfluidic features such as, without limitation, microfluidic channels, chambers, valves, other components within microfluidic devices 204 that are used to transport and/or manipulate at least a fluid on a microscale within apparatus 200.

With continued reference to FIG. 2, exemplary embodiments of at least a sensor device 224 integrated to a passive microfluidic environment is illustrated. In some embodiments, microfluidic environment may include a passive microfluidic environment, wherein the passive microfluidic environment is a microfluidic environment driven by passive flow component. Passive flow component may include any passive flow component as described in this disclosure. In a non-limiting example, flow of at least a fluid within passive microfluidic environment may only include passive flow. Passive microfluidic environment may utilize capillary action or wicking, provided by passive flow component, to flow at least a fluid through microfluidic feature 208 of microfluidic device 204 as described above. In some embodiments, passive flow component may include a capillary pump. As used in this disclosure, a "capillary pump" is a component that operates without any external power source and relies on capillary action to move at least a fluids in fluidic communication with the capillary pump. "Capillary action," for the purpose of this disclosure, is a phenomenon that occurs when a liquid such as, without limitation, at least a fluid, in contact with a solid surface such as, without limitation, sensor interface including porous membrane, and is able to move against gravity due to the combined effects of adhesive and cohesive forces. In a non-limiting example, passive flow process may be initiated as a function of such capillary action. In a non-limiting example, when the porous membrane is in contact with the at least a fluid in a first reservoir, the at least a fluid may be drawn into the pores of the porous membrane due to capillary action. First reservoir may be located at a first layer. A pressure difference may be created across the medium as the last a fluid fills the pores; for instance, and without limitation, pressure may be higher on the side of the porous membrane that is in contact with the at least a fluid. Such pressure difference may cause the at least a fluid to flow through the sensor interface and into a second reservoir, wherein the second reservoir may be located at a second layer, and wherein the first layer is above the second layer, separated by sealer. In some cases, capillary pump may operate continuously, as long as there is a sufficient supply of fluid in first reservoir. Flow properties such as, without limitation, the rate of flow of at least a fluid through capillary pump may be determined by the size and porosity of the porous membrane, the surface tension of the at least a fluid, and the height difference between first reservoir and second reservoir. Additionally, or alternatively, passive microfluidic environment may utilize other microfluidic feature such as, without limitation, a conjugate pad, and a bubble trap, wherein both component will be described in further detail below. Further, in other embodiments, microfluidic environment may include an active microfluidic environment, wherein the active microfluidic environment is a microfluidic environment driven by active flow component. Active flow component may include any active flow component as described in this disclosure. Elements of active flow component are described in further detail below in this disclosure. In such embodiment, active microfluidic environment may utilize a pressure, produced and/or varied by active flow component powered by a power source, to flow at least a fluid through microfluidic feature 208 of microfluidic device 204.

Figure 3A:
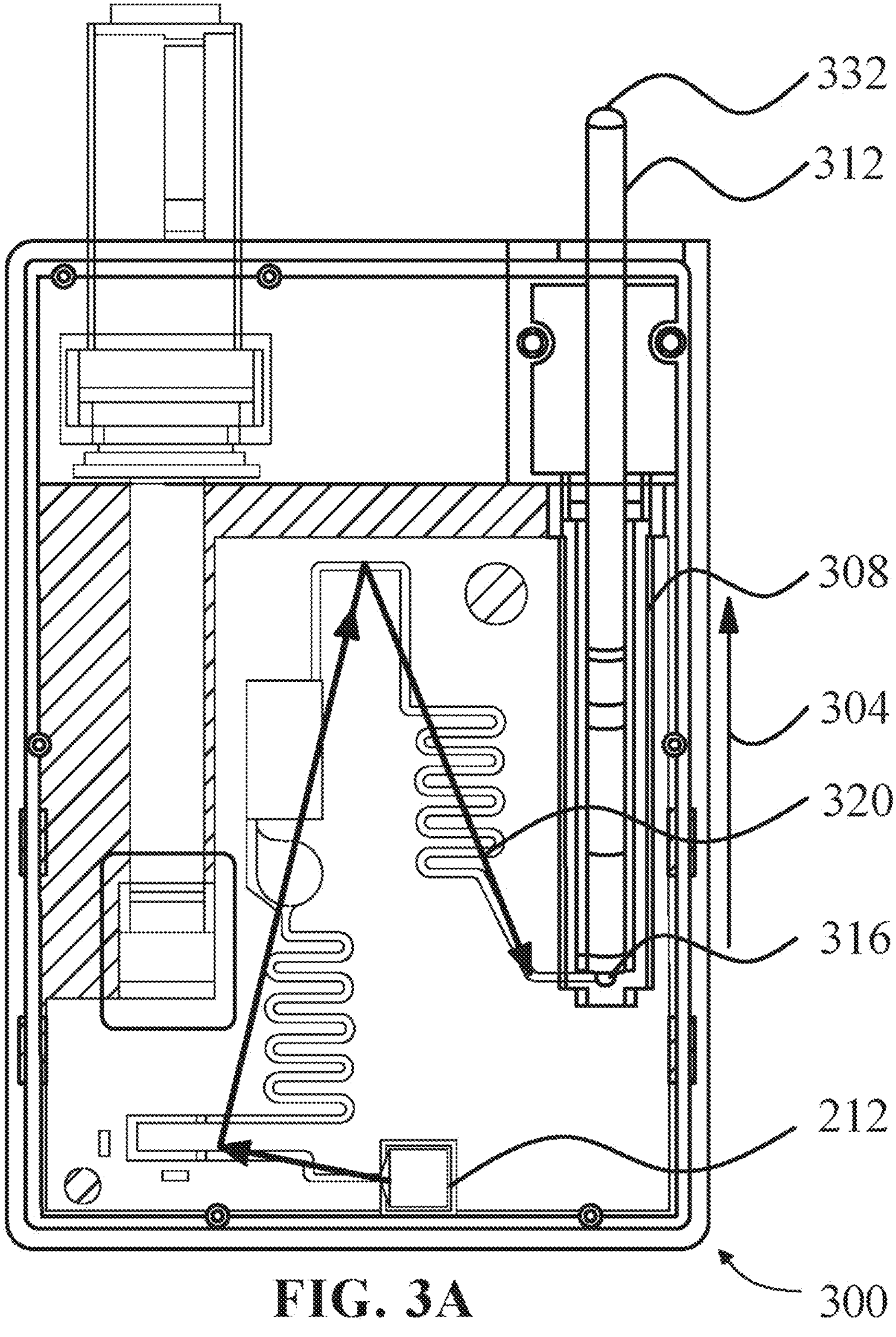
FIGS. 3A-D are diagrams of exemplary embodiments of an active flow component connected to at least a microfluidic feature.

Now referring to FIG. 3A, an exemplary embodiment of an active flow component having a pull regime 304 is illustrated. Active flow component may include a barrel 308 and a plunger 312 inside the barrel 308. As used in this disclosure, a "barrel" is a cylindrical container. A "plunger," as described herein, is a component which can be moved inside the barrel, letting the active flow component draw in at least a fluid through an inlet/outlet 316 of the active flow component. In some cases, inlet/outlet 316 may be connected with microfluidic feature 208 as described above. As used in this disclosure, a "pull regime" is a mode of operation of active flow component configured to create a flow of at least a fluid by actively pulling or drawing at least a fluid through microfluidic feature 208. In a non-limiting example, pull regime 304 may be achieved through pulling plunger 312 within barrel 308 from a first position to a second position, wherein the first position may be before the second position within barrel 308. In some embodiments, active flow component with plunger 312 may include a scaling mechanism, wherein the sealing mechanism may be configured to create a pressure difference between two different areas in active flow component. In some cases, barrel 308 may include an inner diameter equal to the outer diameter of the plunger 312. In a non-limiting example, outer surface of plunger 312 may be in contact with inner surface of the barrel 308, creating a partition within the barrel. Sealing mechanism may enable active flow component to create the partition within barrel 308 with a first pressure different than a second pressure outside the barrel and/or active flow component, wherein the first pressure may be smaller than the second pressure. In some embodiments, active flow process may include a reverse flow process 320. Pull regime 304 may allow for active flow component to initiate the reverse flow process 320. As used in this disclosure, a "reverse flow process" is an active flow process in a reverse direction, wherein the reverse direction is defined as a direction of at least a fluid out of reservoir 208 of microfluid device 204 to inlet/outlet 316 of active flow component. In a non-limiting example, reverse flow process may be initiated as a function of the movement of plunger 312 within barrel 308 from first position to second position in reverse direction.

Figure 3B:
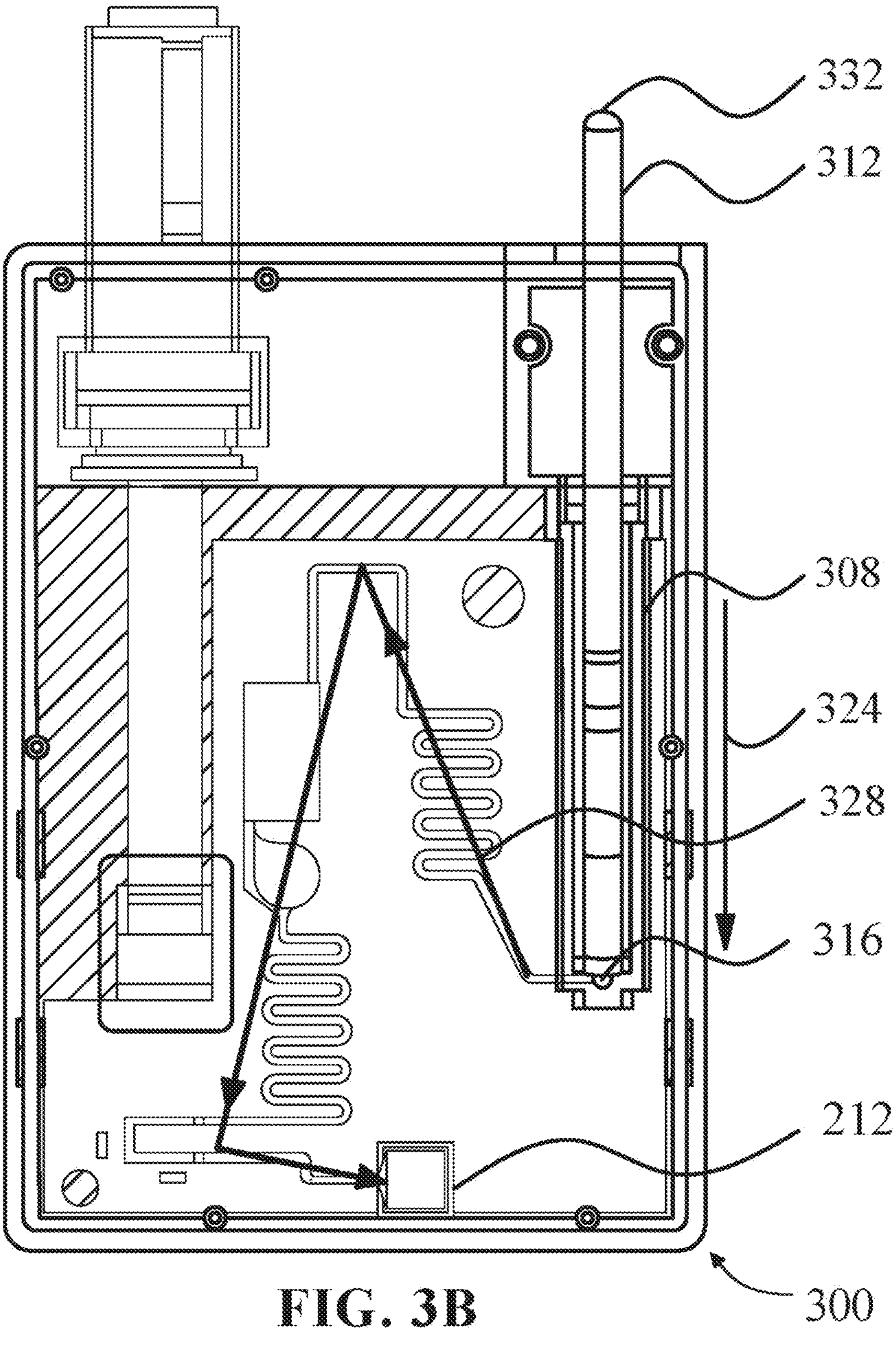

Now referring to FIG. 3B, an exemplary embodiments of active flow component having a push regime 324 is illustrated. As used in this disclosure, a "push regime" is a mode of operation of active flow component configured to create a flow of at least a fluid by actively pushing or expel at least a fluid through microfluidic feature 208. In a non-limiting example, push regime 324 may be achieved through pushing plunger 312 within barrel 308 from the second position back to the first position. Pushing regime 324 may reduce pressure within the partition which leads at least a fluid within the partition to be expelled out of active flow component from inlet/outlet 316 into microfluidic channel 208. In some embodiments, active flow process may include a forward flow process 328. As used in this disclosure, a "forward flow process" is an active flow process in a forward direction, wherein the forward direction is defined as a direction of at least a fluid into reservoir 212 of microfluid device 204 from active flow component. In a non-limiting example, forward flow process 328 may be initiated as a function of the movement of plunger within barrel from second position back to first position in forward direction. The ability to reverse flow (e.g., via pull regime 304 or push regime 324) may allow for any number of assay steps as described below in reference to FIGS. 5-6 (e.g., single, or multi-step assays).

With continued reference to FIGS. 3A-B, pull regime 304 and/or push regime 324 of active flow component may be driven by an actuator, wherein the actuator may be connected to plunger 312 through a mechanical interface 332. As used in this disclosure, an "actuator" is a device that produces a motion by converting energy and signals going into the system. In some cases, motion may include linear, rotatory, or oscillatory motion. Actuator may include a component of a machine that is responsible for moving and/or controlling a mechanism or system. Actuator may, in some cases, require a control signal and/or a source of energy or power. In some cases, a control signal may be relatively low energy. Exemplary control signal forms include electric potential or current, pneumatic pressure or flow, or hydraulic fluid pressure or flow, mechanical force/torque or velocity, or even human power. In some cases, an actuator may have an energy or power source other than control signal. This may include a main energy source, which may include for example electric power, hydraulic power, pneumatic power, mechanical power, and the like. In some cases, upon receiving a control signal, actuator responds by converting source power into mechanical motion. In some cases, actuator may be understood as a form of automation or automatic control. Additionally, or alternatively, actuator may be enclosed by housing 220. In such embodiment, housing 220 may protect actuator from damage by external factors.

With continued reference to FIG. 3A-B, in some embodiments, actuator may include a hydraulic actuator. A hydraulic actuator may consist of a cylinder or fluid motor that uses hydraulic power to facilitate mechanical operation. Output of hydraulic actuator may include mechanical motion as described above. In some cases, hydraulic actuator may employ a liquid hydraulic fluid. As liquids, in some cases. are incompressible, a hydraulic actuator can exert large forces. Additionally, as force is equal to pressure multiplied by area, hydraulic actuators may act as force transformers with changes in area (e.g., cross sectional area of cylinder and/or piston). An exemplary hydraulic cylinder may consist of a hollow cylindrical tube within which a piston can slide. In some cases, a hydraulic cylinder may be considered single acting. Single acting may be used when fluid pressure is applied substantially to just one side of a piston. Consequently, a single acting piston can move in only one direction. In some cases, a spring may be used to give a single acting piston a return stroke. In some cases, a hydraulic cylinder may be double acting. Double acting may be used when pressure is applied substantially on each side of a piston; any difference in resultant force between the two sides of the piston causes the piston to move.

With continued reference to FIGS. 3A-B, in some embodiments, actuator may include a pneumatic actuator. In some cases, a pneumatic actuator may enable considerable forces to be produced from relatively small changes in gas pressure. In some cases, a pneumatic actuator may respond more quickly than other types of actuators, for example hydraulic actuators. A pneumatic actuator may use compressible fluid (e.g., air). In some cases, a pneumatic actuator may operate on compressed air. Operation of hydraulic and/or pneumatic actuators may include control of one or more valves, circuits, fluid pumps, and/or fluid manifolds.

With continued reference to FIGS. 3A-B, in some cases, actuator may include an electric actuator. Electric actuator may include one or more of electromechanical actuators, linear motors, and the like. In some cases, actuator may include an electromechanical actuator. An electromechanical actuator may convert a rotational force of an electric rotary motor into a linear movement to generate a linear movement through a mechanism. Exemplary mechanisms, include rotational to translational motion transformers, such as without limitation a belt, a screw, a crank, a cam, a linkage, a scotch yoke, and the like. In some cases, control of an electromechanical actuator may include control of electric motor, for instance a control signal may control one or more electric motor parameters to control electromechanical actuator. Exemplary non-limitation electric motor parameters include rotational position, input torque, velocity, current, and potential. electric actuator may include a linear motor. Linear motors may differ from electromechanical actuators, as power from linear motors is output directly as translational motion, rather than output as rotational motion and converted to translational motion. In some cases, a linear motor may cause lower friction losses than other devices. Linear motors may be further specified into at least 3 different categories, including flat linear motor, U-channel linear motors and tubular linear motors. Linear motors may be directly controlled by a control signal for controlling one or more linear motor parameters. Exemplary linear motor parameters include without limitation position, force, velocity, potential, and current.

With continued reference to FIGS. 3A-B, in some embodiments, actuator may include a mechanical actuator. In some cases, a mechanical actuator may function to execute movement by converting one kind of motion, such as rotary motion, into another kind, such as linear motion. An exemplary mechanical actuator includes a rack and pinion. In some cases, a mechanical power source, such as a power take off may serve as power source for a mechanical actuator. Mechanical actuators may employ any number of mechanism, including for example without limitation gears, rails, pulleys, cables, linkages, and the like. In a non-limiting example, actuator may include a linear actuator. As used in this disclosure, a "linear actuator" is an actuator that creates linear motion. Linear actuator may create motion in a straight line; for instance, and without limitation, active flow component, particularly, plunger 312 and/or barrel 308 may be aligned with the straight line. Pull regime 304 and/or push regime 324 may be driven by such linear actuator. Actuator may include any actuator described in U.S. patent application Ser. No. 18/107,135.

With continued reference to FIGS. 3A-B, a "mechanical interface," for the purpose of this disclosure, is a component configured to connect at least two components. In an embodiment, mechanical interface 332 between plunger 312 and actuator may be a friction fit, an interference fit, or a snap fit, wherein plunger 312 may include a male or female adapter and the actuator 220 may include a female or male adapter. For example, and without limitation, when the male (female) adapter engages with the female (male) adapter a mechanical connection is established. This mechanical connection can be designed so that it automatically disengages when a certain level of force is applied. Alternatively, it can be designed so that a mechanical input is necessary to cause the male and female connectors to disengage. In some embodiments, this mechanical coupling between plunger 312 and actuator may be accomplished by other means (e.g., a Janney coupler, knuckle coupler, etc.). In other embodiments, mechanical coupling between plunger 312 and actuator may be accomplished by a magnet or multiple magnets.

Figure 3C:
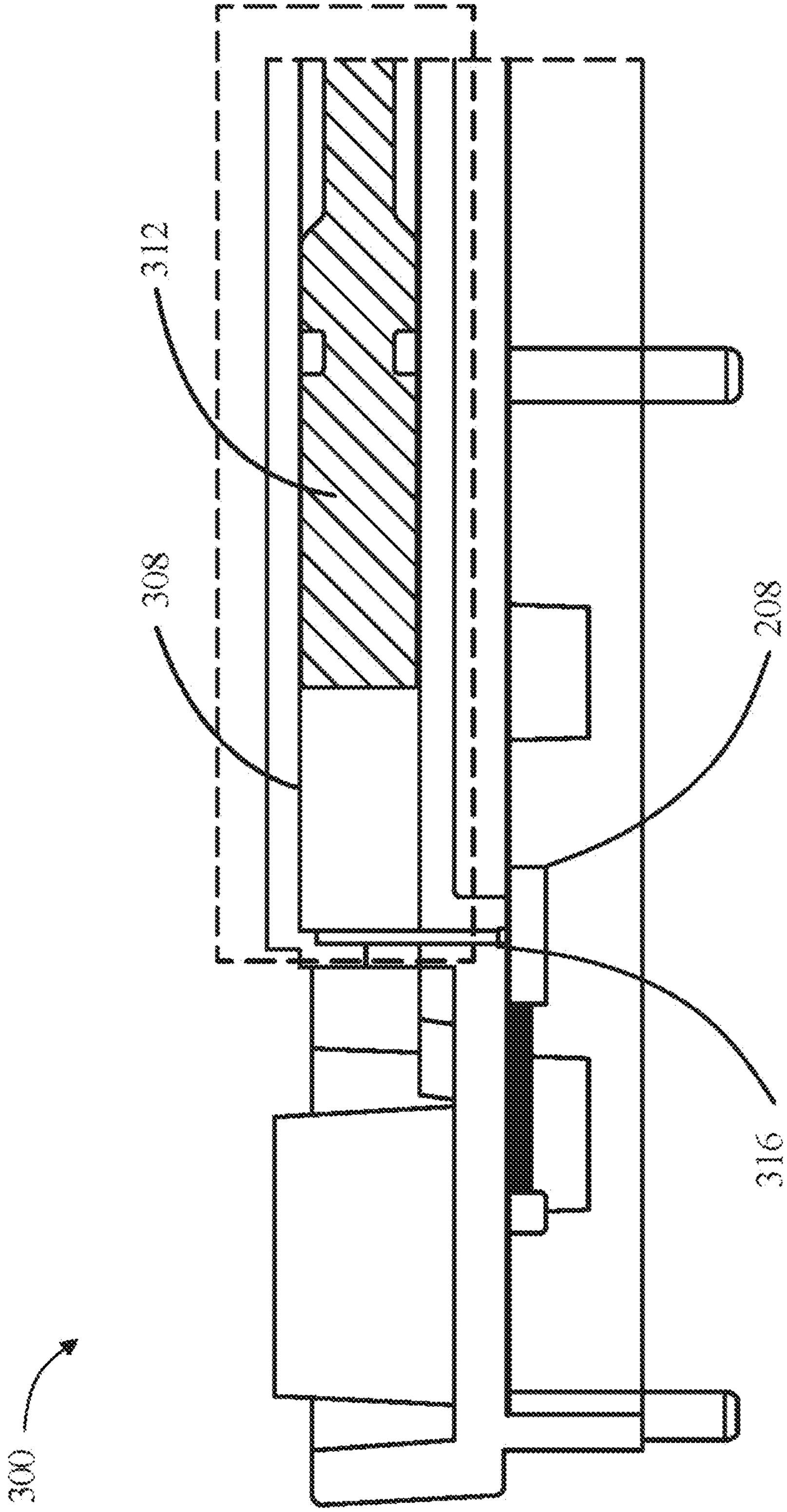
Figure 3D:
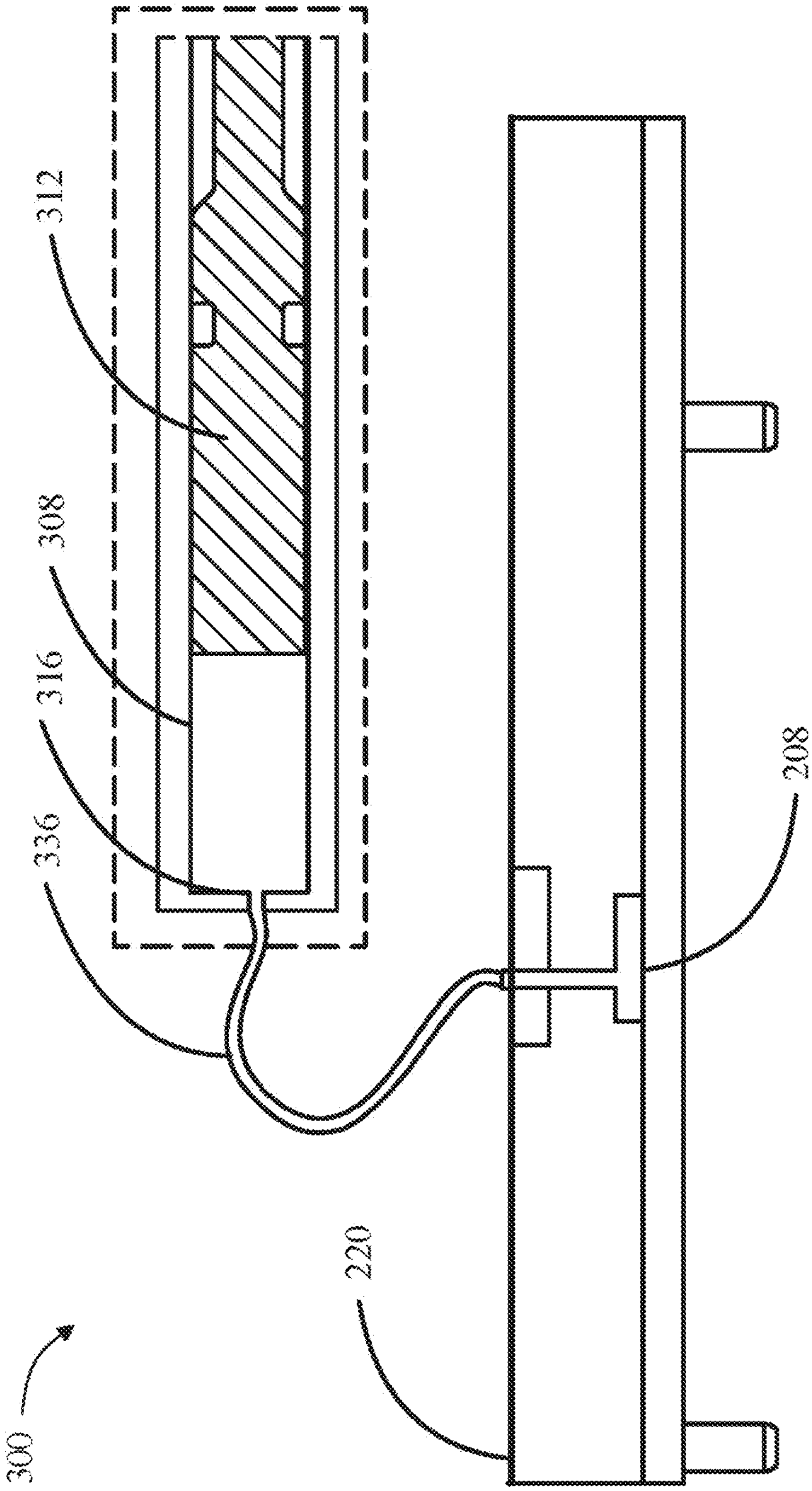

Now referring to FIGS. 3C-D, exemplary embodiments of active flow component connected to at least a microfluidic feature 208 are illustrated. In some embodiment, active flow component may be integrated within apparatus 200 (as shown in FIG. 3C). Inlet/outlet 316 of active flow component may be connected to at least a microfluidic feature 208 such as, without limitation, microfluidic channel. In some case, at least a fluid may flow from at least a microfluidic feature 208 through inlet 316 into active flow component during reverse flow process 320 initiated by pull regime 304 as described above. In other cases, at least a fluid may flow from active flow component through outlet 316 into at least a microfluidic feature 208 during forward flow process 228 initiated by push regime 324 as described above. Additionally, or alternatively, active flow component may not be integrated within apparatus 200 but may have a connection with at least a microfluidic feature 208 (as shown in FIG. 3B). In a non-limiting example, active flow component may be disposed on the exterior of apparatus 200. A tube 336 may be used to connect fluidically active flow component to apparatus 200. For the purpose of this disclosure, a "tube" is a hollow cylindrical component configured to transport at least a fluid. In some cases, tube 336 may be flexible; for instance, tube may be made of plastic. In a non-limiting example, one end of tube 336 may be connected with inlet/outlet 316 of active flow component and another end of tube 336 may be connected with at least a microfluidic feature 336. In other cases, tube 336 may include an external extension of microfluidic feature 208.

Figure 4:
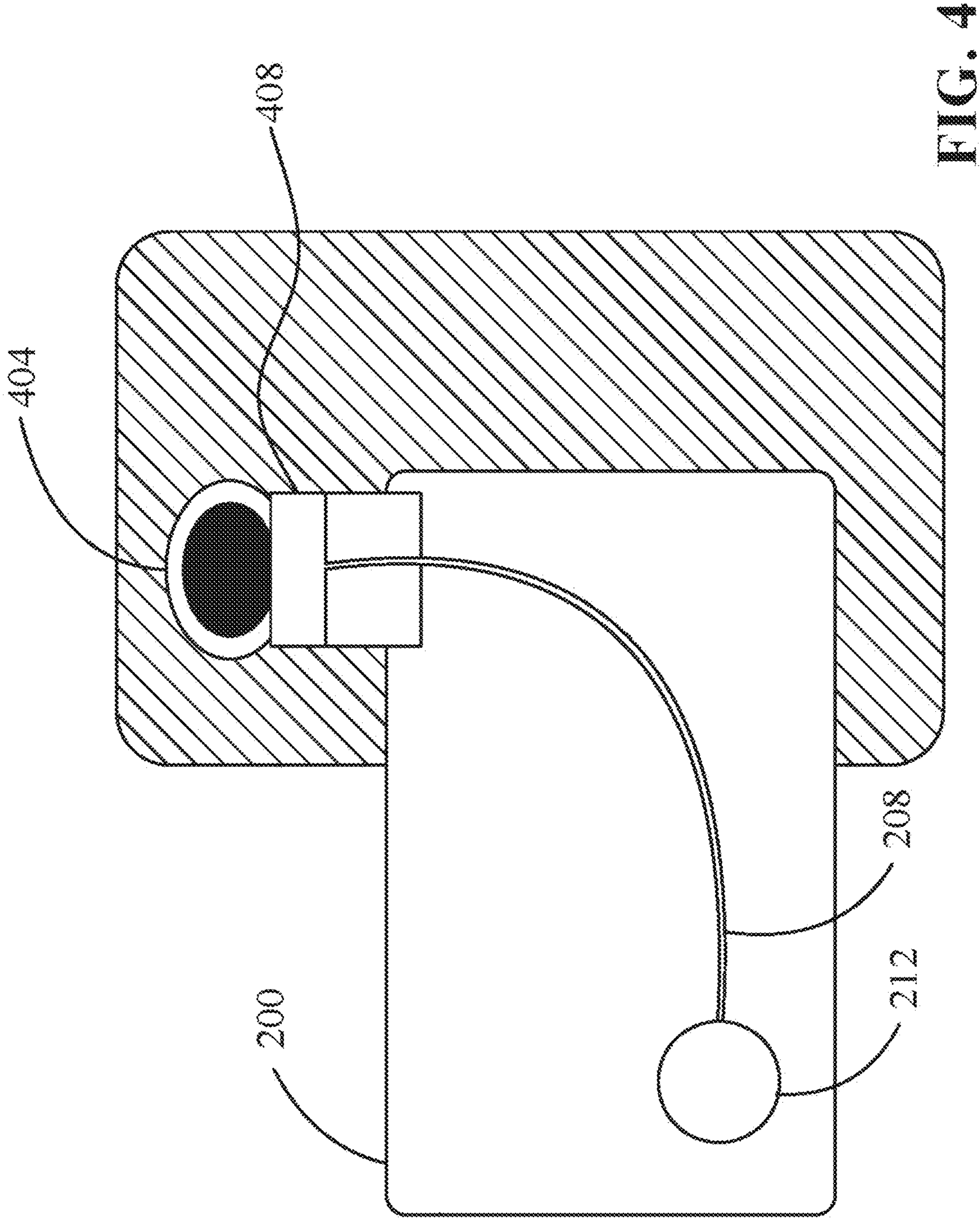
FIG. 4 is an exemplary embodiment of a liquid pump integrated on external device.

Now referring to FIG. 4, an exemplary embodiment of a liquid pump 404 integrated on external device is illustrated. In some embodiments, active flow component may be integrated within external device. In a non-limiting example, active flow component may include a liquid pump 404, wherein the liquid pump 404 may be integrated within external device and connected to at least a microfluidic feature 208 of apparatus 200 through a pump interface 408. Liquid pump may include any pump described in this disclosure. In some embodiments, liquid pump 404 may be configured to transport at least a fluid from one location to another by means of mechanical or electrical energy; for instance, and without limitation, liquid pump 404 may be configured to transport at least a fluid from reservoir 212 to pump interface 408, or another way around, wherein the "pump interface," for the purpose of this disclosure, is a mechanism that connects liquid pump 404 to at least a microfluidic feature 208 such as, without limitation, microfluidic channel, reservoir 212, and the like thereof. In some embodiments, pump interface 408 may include, without limitation, piping, valves, flanges, connectors, fittings, and/or any other components that are configured to ensure a secure and reliable connection between liquid pump 404 and microfluidic feature 208. Additionally, or alternatively, apparatus 200 may utilize passive flow component (i.e., capillary action and wicking) to drive fluid flow while apparatus 200 is connected to external device 504 as described above.

Figure 5:
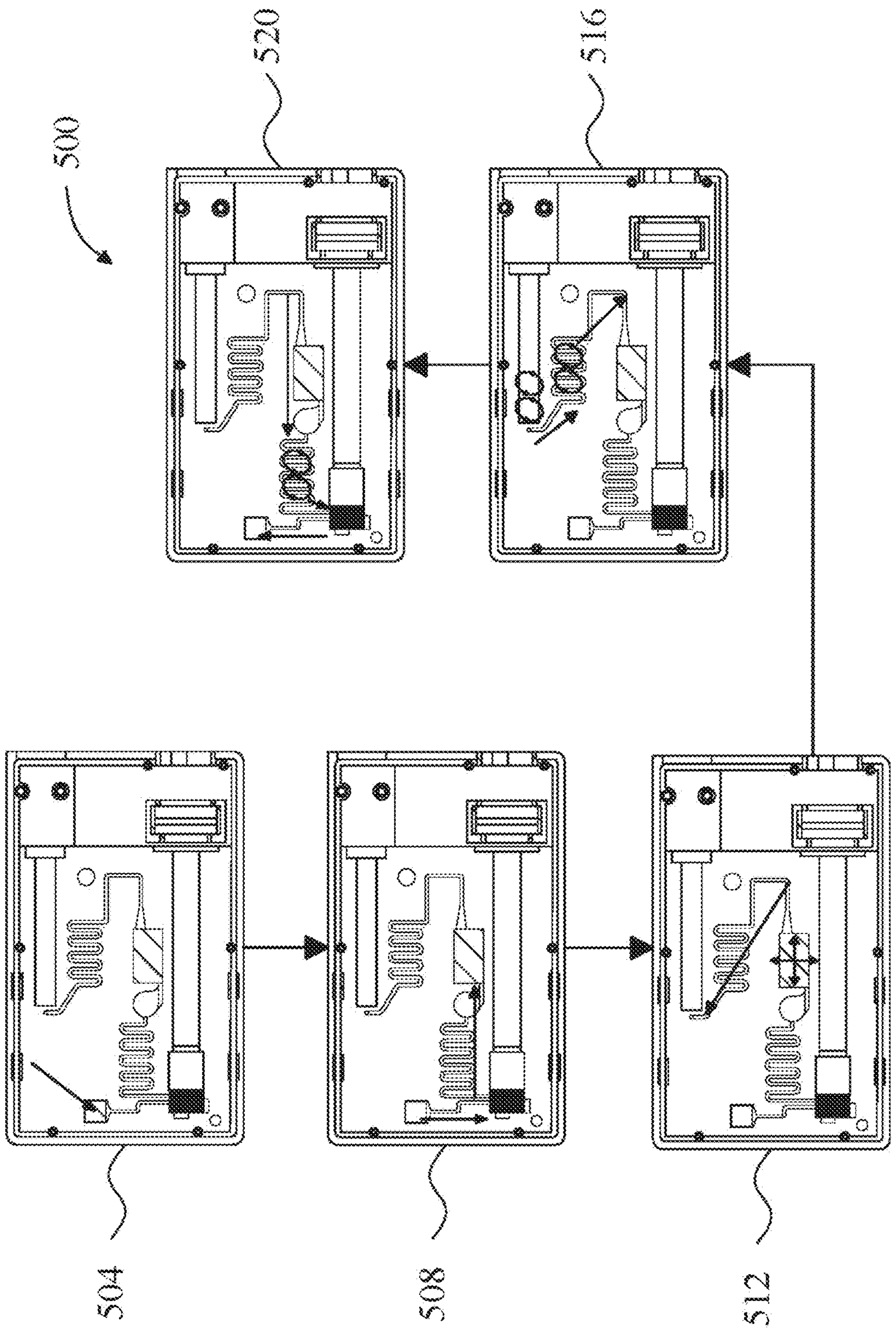
FIG. 5 is an exemplary embodiment of a two-step assay.

Now referring to FIG. 5, an exemplary embodiment of a two-step assay 500 performed using apparatus 200 is illustrated. Two-step assay 500 may include a step 504 of adding a sample into reservoir 212. Two-step assay 500 may include a step 508 of flowing the sample to conjugate pad as a function of a reverse flow process initiated by active flow component using pull regime 304. Two-step assay 500 may include a step 512 of releasing a conjugate regent stored in conjugate pad. Two-step assay 500 may include a step of 516 of flowing the sample and conjugate regent as a function of forward flow process initiated by active flow component using push regime 324, wherein flowing the sample and conjugate regent may further include mixing conjugate regent and sample within barrel 308 of active flow component and/or microfluidic feature 208 after and/or before conjugate pad. Two-step assay 500 may further include a step 520 of flowing the mixture of sample and conjugate regent through sensor device 224 and back to reservoir 212.

Figure 6:
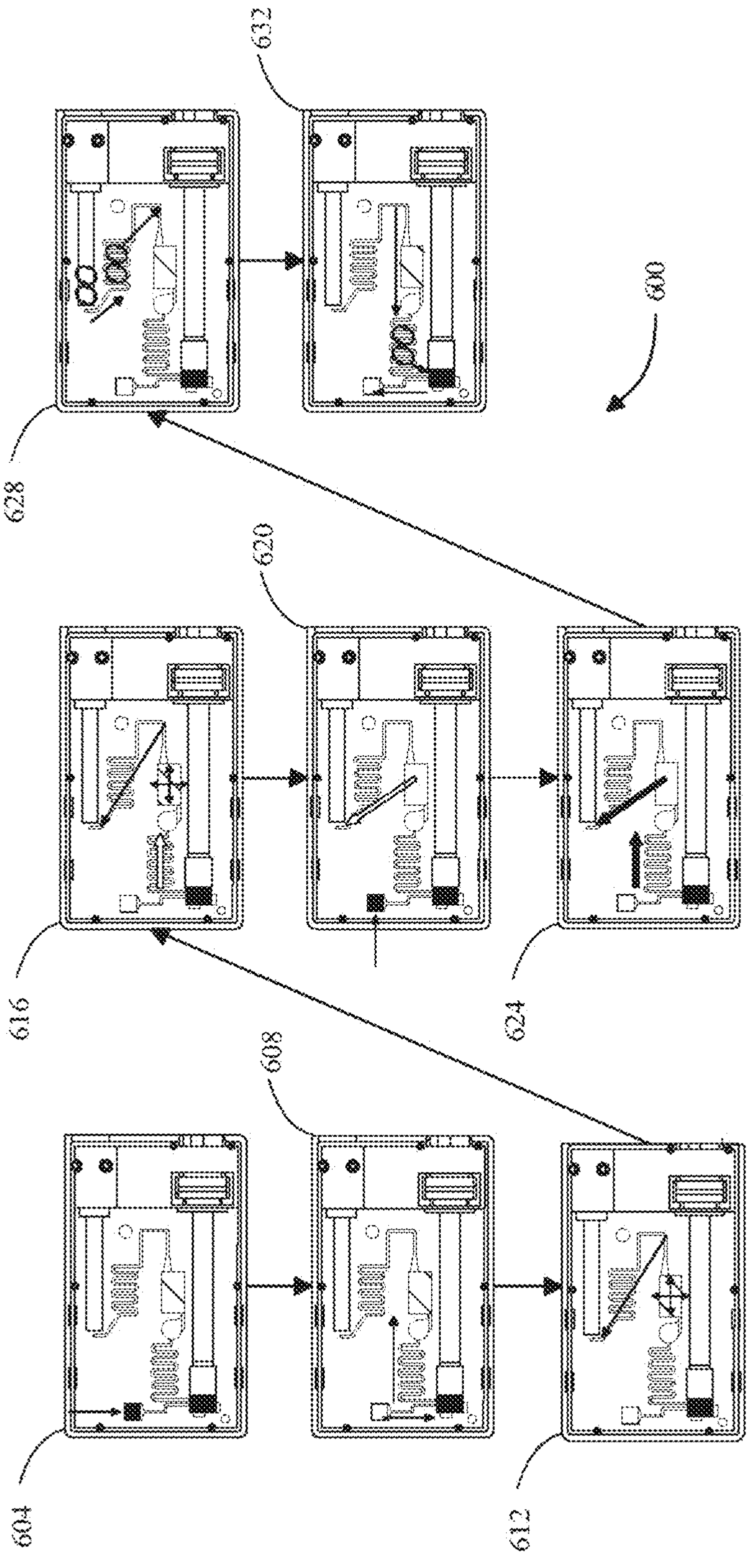
FIG. 6 is an exemplary embodiment of a three-step assay.

Now referring to FIG. 6, an exemplary embodiment of a three-step assay 600 performed using apparatus 200 is illustrated. Three-step assay 600 may include a step 604 of adding a sample into reservoir 212. Three-step assay 600 may include a step 608 of flowing the sample to conjugate pad as a function of a reverse flow process initiated by active flow component using pull regime 304. Three-step assay 600 may include a step of releasing a conjugate regent stored in conjugate pad. Three-step assay 600 may include a step 616 of adding a buffer fluid, driven by pull regime 304. Three-step assay 600 may include a step 620 of receiving buffer fluids, sample, and conjugate regent at active flow component. Three-step assay 600 may include a step 624 of utilizing an air bubble as a separation barrier between buffer fluid and any regents added later. Three-step assay 600 may include a step 628 of flowing received fluids (i.e., pre-mixed regents, conjugate reagent, and sample buffer) as a function of forward flow process initiated by active flow component using push regime 324, wherein flowing the fluids may further include mixing fluids within barrel 308 of active flow component and/or microfluidic features 208 after and/or before conjugate pad. Three-step assay 600 may further include a step 632 of flowing the mixture through sensor device 224 and back to reservoir 212.

Figure 7:
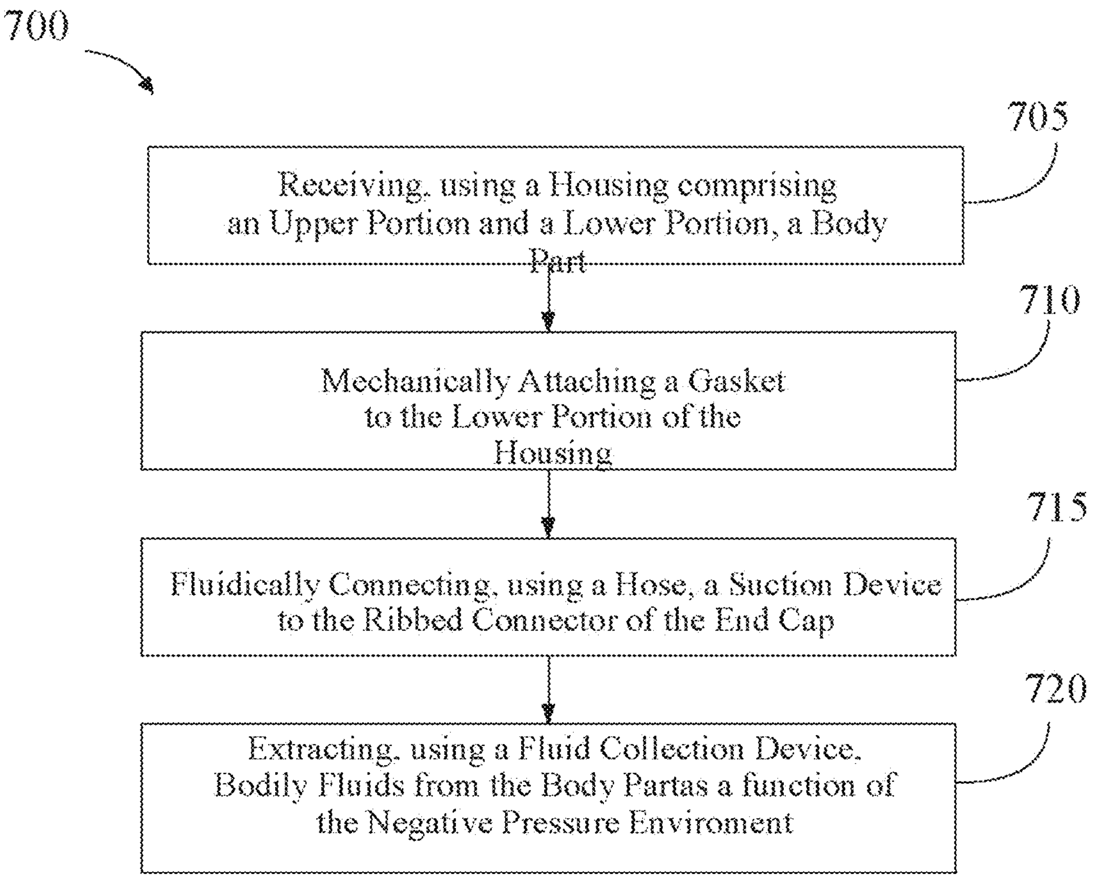
FIG. 7 is a flow diagram of an exemplary method for the extraction and collection of bodily fluids.

Referring now to FIG. 7, a flow diagram of an exemplary method 700 for the extraction and collection of bodily fluids is illustrated. At step 705, method 700 includes receiving, using housing comprising an upper portion and a lower portion, a body part. This may be implemented as described and with reference to FIGS. 1-7. In an embodiment, the method further includes puncturing, using a lancet, the skin of the body part, wherein the lancet is removably attached to the end cap. In an embodiment, the end cap may include an adjustable height feature. In an embodiment, the housing further comprises a protruded brim configured to mate with the gasket. In another embodiment, the housing is configured to have a cylindrical geometry.

Still referring to FIG. 7, at step 710, method 700 includes mechanically attaching a gasket to the lower portion of the housing, wherein the gasket is configured to form an airtight seal between the body part and the housing. This may be implemented as described and with reference to FIGS. 1-7.

Still referring to FIG. 7, at step 715, method 700 includes fluidically connecting, using a hose, a suction device to the ribbed connector of the end cap, wherein the suction device is configured to create a negative pressure environment within the housing. This may be implemented as described and with reference to FIGS. 1-7. In an embodiment, the suction device may include an automatic suction device and/or a manual pump.

Still referring to FIG. 7, at step 720, method 700 includes extracting, using a fluid collection device, bodily fluids from the body part as a function of the negative pressure environment, wherein the fluid collection is removably attached to the end cap. This may be implemented as described and with reference to FIGS. 1-7. In an embodiment, a fluid collection device may include a fluid collection pad. In another embodiment, the method further includes fluidically connecting the fluid collection device to at least a reservoir of a microfluidic device. The microfluidic device may include at least a microfluidic feature and at least an alignment feature for attaching a sensor device to the microfluidic device.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
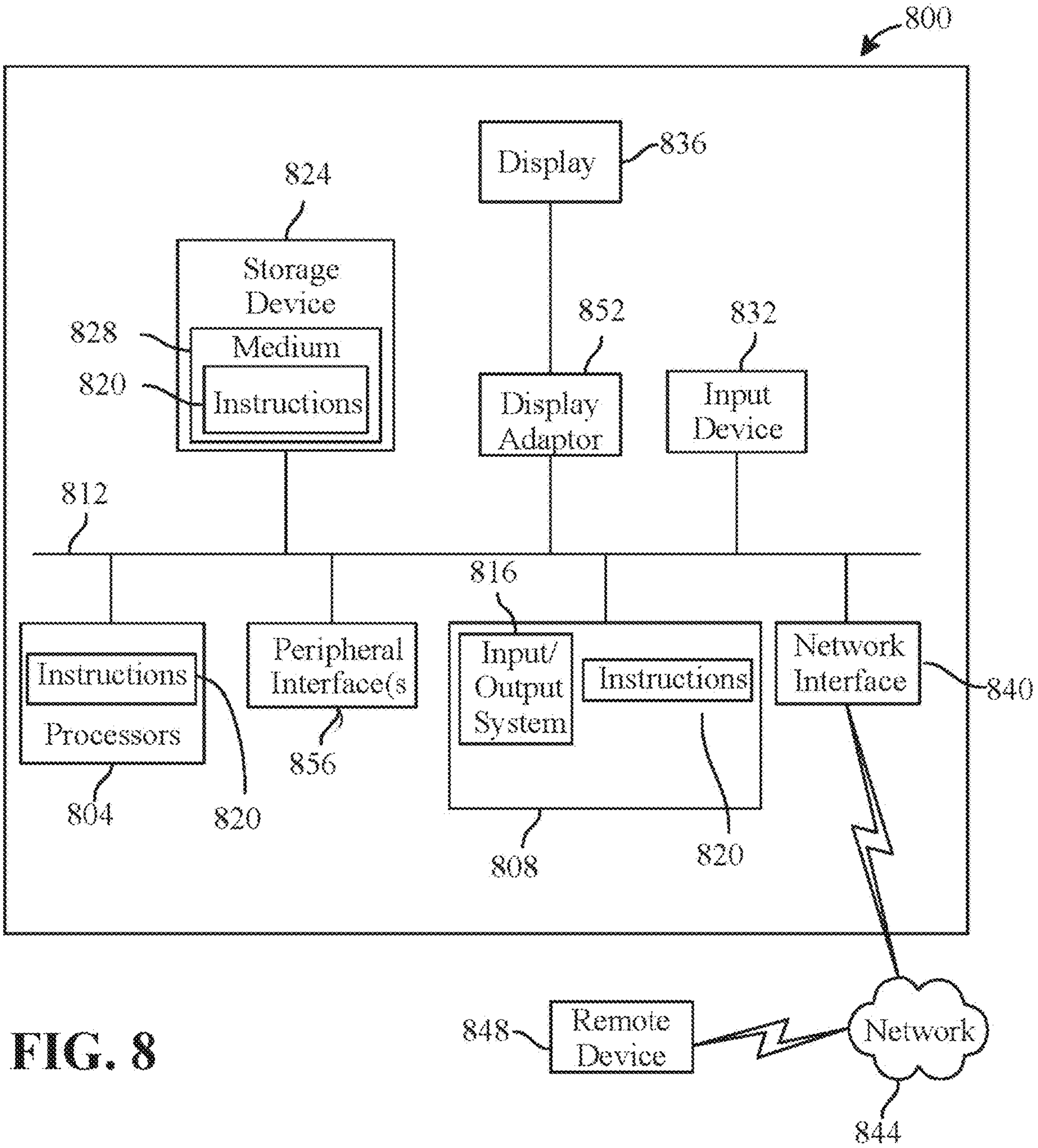
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. An apparatus for the extraction and collection of bodily fluids, wherein the apparatus comprises:

a housing configured to receive a body part, wherein the housing comprises an upper portion and a lower portion, wherein the housing further comprises:

an end cap removably attached to the upper portion of the housing, wherein the end cap comprises a ribbed connector; and a first aperture located on the lower portion of the housing;

a gasket mechanically attached to the lower portion of the housing, wherein the gasket is configured to form an airtight seal between the body part and the housing;

a suction device fluidically connected to the ribbed connector of the end cap using a hose, wherein the suction device is configured to create a negative pressure environment within the housing; and a fluid collection device configured to extract bodily fluids from the body part as a function of the negative pressure environment, wherein the fluid collection device is removably attached to the end cap.

2. The apparatus of claim 1, wherein the apparatus further comprises a lancet configured to puncture the skin of the body part, wherein the lancet is removably attached to the end cap.

3. The apparatus of claim 2, wherein the lancet comprises a spring-loaded lancet.

4. The apparatus of claim 1, wherein the end cap comprises an adjustable height feature.

5. The apparatus of claim 1, wherein the housing comprises a cylindrical geometry.

6. The apparatus of claim 1, wherein the suction device comprises a manual pump.

7. The apparatus of claim 1, wherein the suction device comprises an automatic suction device.

8. The apparatus of claim 1, wherein the fluid collection device comprises a fluid collection pad.

9. The apparatus of claim 1, wherein the fluid collection device is fluidically connected to at least a reservoir of a microfluidic device.

10. The apparatus of claim 9, wherein the microfluidic device further comprises:

at least a microfluidic feature; and at least an alignment feature for attaching a sensor device to the microfluidic device.

11. A method for the extraction and collection of bodily fluids, wherein the method comprises:

receiving, using a housing comprising an upper portion and a lower portion, a body part, wherein the housing further comprises:

an end cap removably attached to the upper portion of the housing, wherein the end cap comprises a ribbed connector; and a first aperture located on the lower portion of the housing;

mechanically attaching a gasket to the lower portion of the housing, wherein the gasket is configured to form an airtight seal between the body part and the housing;

fluidically connecting, using a hose, a suction device to the ribbed connector of the end cap, wherein the suction device is configured to create a negative pressure environment within the housing; and extracting, using a fluid collection device, bodily fluids from the body part as a function of the negative pressure environment, wherein the fluid collection device is removably attached to the end cap.

12. The method of claim 11, wherein the method further comprises puncturing, using a lancet, the skin of the body part, wherein the lancet is removably attached to the end cap.

13. The method of claim 12, wherein the lancet comprises a spring-loaded lancet.

14. The method of claim 11, wherein the end cap comprises an adjustable height feature.

15. The method of claim 11, wherein the housing comprises a cylindrical geometry.

16. The method of claim 11, wherein the suction device comprises a manual pump.

17. The method of claim 11, wherein the suction device comprises an automatic suction device.

18. The method of claim 11, wherein the fluid collection device comprises a fluid collection pad.

19. The method of claim 11, wherein the method further comprises fluidically connecting the fluid collection device to at least a reservoir of a microfluidic device.

20. The method of claim 19, wherein the microfluidic device further comprises:

at least a microfluidic feature; and at least an alignment feature for attaching a sensor device to the microfluidic device.

* * * * *